United States Patent
Son et al.

(10) Patent No.: US 11,559,555 B2
(45) Date of Patent: Jan. 24, 2023

(54) CRUDE DRUG COMPOSITION FOR PREVENTING OR TREATING RESPIRATORY DISEASES

(71) Applicant: HELIXMITH CO., LTD., Seoul (KR)

(72) Inventors: Mi Won Son, Gyeonggi-do (KR); Min Jung Bae, Jeollabuk-do (KR); Won Woo Lee, Seoul (KR); Doo Suk Lee, Gyeonggi-do (KR)

(73) Assignee: HELIXMITH CO., LTD., Seoul (KR)

( * ) Notice: Subject to any disclaimer, the term of this patent is extended or adjusted under 35 U.S.C. 154(b) by 0 days.

(21) Appl. No.: 16/980,983

(22) PCT Filed: Mar. 15, 2019

(86) PCT No.: PCT/KR2019/003062
§ 371 (c)(1),
(2) Date: Sep. 15, 2020

(87) PCT Pub. No.: WO2019/177428
PCT Pub. Date: Sep. 19, 2019

(65) Prior Publication Data
US 2020/0405798 A1     Dec. 31, 2020

(30) Foreign Application Priority Data

Mar. 16, 2018  (KR) .................. 10-2018-0031151
Nov. 29, 2018  (KR) .................. 10-2018-0150900
Mar. 13, 2019  (KR) .................. 10-2019-0028959

(51) Int. Cl.
| | | |
|---|---|---|
| *A61K 36/31* | (2006.01) | |
| *A23L 33/105* | (2016.01) | |
| *A61P 11/06* | (2006.01) | |
| *A61P 11/16* | (2006.01) | |
| *A61K 9/00* | (2006.01) | |
| *A61K 36/342* | (2006.01) | |
| *A61K 36/35* | (2006.01) | |
| *A61K 36/53* | (2006.01) | |

(52) U.S. Cl.
CPC ............ *A61K 36/31* (2013.01); *A23L 33/105* (2016.08); *A61K 9/0053* (2013.01); *A61K 36/342* (2013.01); *A61K 36/35* (2013.01); *A61K 36/53* (2013.01); *A61P 11/06* (2018.01); *A61P 11/16* (2018.01); *A61K 2236/331* (2013.01); *A61K 2236/333* (2013.01)

(58) Field of Classification Search
None
See application file for complete search history.

(56) References Cited

FOREIGN PATENT DOCUMENTS

| CN | 1528391 A | 9/2004 |
|---|---|---|
| CN | 102284025 A | 12/2011 |
| CN | 104306908 A | 1/2015 |
| CN | 106237056 A | 12/2016 |
| CN | 106729562 A | 5/2017 |
| EP | 2450046 A1 | 5/2012 |
| JP | 2004-83449 A | 3/2004 |
| KR | 10-2000-0051511 A | 8/2000 |
| KR | 10-2003-0007243 A | 1/2003 |
| KR | 10-2012-0034770 A | 4/2012 |
| KR | 10-2013-0062245 A | 6/2013 |
| KR | 10-1569876 B1 | 11/2015 |
| KR | 10-2016-0045368 A | 4/2016 |
| KR | 10-2017-0115852 A | 10/2017 |
| WO | WO-2011-000150 A1 | 1/2011 |
| WO | WO-2013-081425 A1 | 6/2013 |

OTHER PUBLICATIONS

International Search Report from corresponding PCT Application No. PCT/KR2019/003062, dated Jul. 12, 2019, with English translation.
Clinical Medication Instructions, Pharmacopoeia of the People's Republic of China, the edition in 2015, the volume of Traditional Chinese Herbal Pieces for Decoction, Chinese Medicine Science and technology Publishing House, the 1st edition, 2017-09, p. 918.
Office Action of CN Patent Application No. 201980019846.0, dated Jul. 30, 2021.
Office Action of JP Patent Application No. 2020-549811, dated Aug. 27, 2021.
ESR of EP Patent Application No. 19768114.1 dated Mar. 22, 2021.
Roh, S., et al.; "Effects of Radix Adenophorae and Cyclosporine A on an OVA-Induced Murine Model of Asthma by Suppressing to T Cells Activity, Eosinophilia, and Bronchial Hyperresponsiveness", Mediators of Inflammation, vol. 2008, 11 pages.
Ryu, K., et al.; "Anti-asthmatic Activites of the Extract of *Lonicera japonica*", Korean Journal of Pharmacognosy, 1999, vol. 30, No. 4, pp. 377-383.

(Continued)

*Primary Examiner* — Susan Hoffman
(74) *Attorney, Agent, or Firm* — Harness, Dickey & Pierce, P.L.C.

(57) ABSTRACT

The present disclosure relates to a pharmaceutical composition for preventing or treating respiratory diseases and a food composition for preventing or relieving respiratory diseases comprising as an active ingredient two or more mixed extracts selected from the group consisting of a Brassicae Semen extract, an Adenophorae Radix extract, a Lonicerae Folium extract and a Perillae Semen extract. A composition comprising mixed extracts of Brassicae Semen, Adenophorae Radix, Lonicerae Folium and Perillae Semen of the present disclosure has an advantage of preventing respiratory diseases and relieving the symptoms of respiratory diseases, restores damages in the lung tissue, inhibits aging action and inflammation induced by inflammation-inducing substances such as fine dust, and has an excellent antioxidant effect. More particularly, the composition of the present disclosure increases the expression of a telomerase which extends the length of a telomere.

4 Claims, 18 Drawing Sheets

Specification includes a Sequence Listing.

(56) References Cited

OTHER PUBLICATIONS

Kim, M., et al.; "Asthma diagnosis and treatment—1006. Perillae semen abolished allergic asthmatic response in murine model", World Allergy Organization Journal, 2013, 6.

Office Action from corresponding Japanese Patent Application No. 2020-549811, dated Oct. 25, 2022.

|  | Normal group | Negative control group | Test group |
|---|---|---|---|
| Complex herbal medicine extract(200 μg/mL) | - | - | + |
| PM10(50 μg/mL) | - | + | + |

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Forward primer for GAPDH

<400> SEQUENCE: 1
agcctcgtcc cgtagacaa                    19

<210> SEQ ID NO 2
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 2
aatctccact ttgccactgc                   20

<210> SEQ ID NO 3
<211> LENGTH: 21
<212> TYPE: DNA
<213> ORGANISM: Artificial Sequence
<220> FEATURE:
<223> OTHER INFORMATION: Forward primer for IL-6

<400> SEQUENCE: 3
ttggtcctta gccactcctt c                 21

<210> SEQ ID NO 4
<211> LENGTH: 23
<212> TYPE: DNA
<213> ORGANISM: Artificial Sequence
<220> FEATURE:
<223> OTHER INFORMATION: Reverse primer for IL-6

<400> SEQUENCE: 4
tagtccttcc taccccaatt tcc               23

<210> SEQ ID NO 5
<211> LENGTH: 21
<212> TYPE: DNA
<213> ORGANISM: Artificial Sequence
<220> FEATURE:
<223> OTHER INFORMATION: Forward primer for IL-1beta

<400> SEQUENCE: 5
tgtgcaagtg tctgaagcag c                 21

<210> SEQ ID NO 6
<211> LENGTH: 20
<212> TYPE: DNA
<213> ORGANISM: Artificial Sequence
<220> FEATURE:
<223> OTHER INFORMATION: Reverse primer for IL-1beta

<400> SEQUENCE: 6
tggaagcagc ccttcatctt                   20

<210> SEQ ID NO 7
<211> LENGTH: 19
<212> TYPE: DNA
<213> ORGANISM: Artificial Sequence

```
<220> FEATURE:
<223> OTHER INFORMATION: Forward primer for iNOS

<400> SEQUENCE: 7
cgaaacgctt cacttccaa                                                   19

<210> SEQ ID NO 8
<211> LENGTH: 21
<212> TYPE: DNA
<213> ORGANISM: Artificial Sequence
<220> FEATURE:
<223> OTHER INFORMATION: Reverse primer for iNOS

<400> SEQUENCE: 8
tgagcctata ttgctgtggc t                                                21

<210> SEQ ID NO 9
<211> LENGTH: 20
<212> TYPE: DNA
<213> ORGANISM: Artificial Sequence
<220> FEATURE:
<223> OTHER INFORMATION: Forward primer for HO-1

<400> SEQUENCE: 9
caggtgatgc tgacagagga                                                  20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for HO-1

<400> SEQUENCE: 10
gagagtgagg acccactgga                                                  20

<210> SEQ ID NO 11
<211> LENGTH: 21
<212> TYPE: DNA
<213> ORGANISM: Artificial Sequence
<220> FEATURE:
<223> OTHER INFORMATION: Forward primer for TNF-alpha

<400> SEQUENCE: 11
aagcctgtag cccacgtcgt a                                                21

<210> SEQ ID NO 12
<211> LENGTH: 24
<212> TYPE: DNA
<213> ORGANISM: Artificial Sequence
<220> FEATURE:
<223> OTHER INFORMATION: Reverse primer for TNF-alpha

<400> SEQUENCE: 12
ggcaccacta gttggttgtc tttg                                             24
```

CRUDE DRUG COMPOSITION FOR PREVENTING OR TREATING RESPIRATORY DISEASES

CROSS-REFERENCE TO RELATED APPLICATIONS

This application is a national phase application of PCT Application No. PCT/KR2019/003062, filed on Mar. 15, 2019, which claims the benefit of and priority to Korean Patent Application No. 10-2019-0028959, filed Mar. 13, 2019, Korean Patent Application No. 10-2018-0150900, filed Nov. 29, 2018 and Korean Patent Application No. 10-2018-0031151, filed Mar. 16, 2018. The entire disclosures of the applications identified in this paragraph are incorporated herein by references.

FIELD

The present disclosure relates to a herbal medicine composition for prevention or treatment of a respiratory disease and, specifically, to a composition for prevention, treatment, or alleviation of a respiratory disease, the composition comprising a mixed extract of two or more selected from the group consisting of a Brassicae Semen extract, an Adenophorae Radix extract, a Lonicerae Folium extract, and a Perillae Semen extract.

BACKGROUND

Respiratory diseases are diseases in connection with the lungs and airways, and may be mainly caused by lowered immunity, inflammatory actions, bacterial or viral infections, inhalation of harmful particles due to fine dust or smoking, aging, and the like. Representative respiratory diseases include pneumonia, rhinitis, asthma, bronchitis, tuberculosis, chronic obstructive pulmonary disease (COPD), and the like. Particularly, chronic obstructive pulmonary disease patients are recently increasing due to an increase in fine dust, smoking, and the like. Chronic obstructive pulmonary disease is also called emphysema or chronic bronchitis.

Medicines for such respiratory diseases are being developed mainly targeting anti-inflammatory actions or airway dilation effects. Examples of respiratory disease medicines showing anti-inflammatory and airway dilation effects are glucocorticoid steroid drugs, beta$_2$-adrenergic receptor agonists, leukotriene receptor antagonists, and phosphodiesterase-4 inhibitors (PDE4 inhibitors). However, the therapeutic purposes of these existing respiratory disease medicines are restricted to allergic asthma in infants or children and chronic obstructive pulmonary disease (COPD) in smokers. Moreover, most of the medicines are used for only a purpose of relieving symptoms, and have a limitation in that the medicines fail to delay or stop the progression of respiratory diseases through the removal of fundamental causes of the respiratory diseases. Since most of respiratory diseases have complicated causes and symptoms, existing medicines using a single component or a single therapeutic mechanism cannot obtain suitable therapy. Accordingly, there is an urgent need to develop a novel medicine for preventing and treating a respiratory disease more diversely and complexly.

PRIOR ART DOCUMENTS

Korean Patent Publication No. 10-2017-0115852
Korean Patent Registration No. 10-1569876

SUMMARY

Technical Problem

The present inventors have made research efforts for developing a respiratory disease medicine having a novel therapeutic mechanism to overcome the above-described limitations of existing respiratory disease medicines. As a result, the present inventors verified that a complex herbal medicine extract (mixed extract) of Brassicae Semen, Adenophorae Radix, Lonicerae Folium, and Perillae Semen inhibits inflammation and aging induced by fine dust as well as lung tissue damage and has an excellent antioxidative effect, and thus have completed the present disclosure.

Accordingly, an aspect of the present disclosure is to provide a pharmaceutical composition for prevention or treatment of a respiratory disease, the pharmaceutical composition comprising: as an active ingredient, a mixed extract of two or more selected from the group consisting of a Brassicae Semen extract, an Adenophorae Radix extract, a Lonicerae Folium extract, and a Perillae Semen extract; and a pharmaceutically acceptable carrier.

Another aspect of the present disclosure is to provide a food composition for prevention or alleviation of a respiratory disease, the food composition comprising, as an active ingredient, a mixed extract of two or more selected from the group consisting of a Brassicae Semen extract, an Adenophorae Radix extract, a Lonicerae Folium extract, and a Perillae Semen extract.

Technical Solution

In accordance with an aspect of the present disclosure, there is provided a pharmaceutical composition for prevention or treatment of a respiratory disease, the pharmaceutical composition including: (a) as an active ingredient, a mixed extract of two or more selected from the group consisting of a Brassicae Semen extract, an Adenophorae Radix extract, a Lonicerae Folium extract, and a Perillae Semen extract; and (b) a pharmaceutically acceptable carrier.

Since the mixed extract is a mixed extract of two or more selected from the group consisting of a Brassicae Semen extract, an Adenophorae Radix extract, a Lonicerae Folium extract, and a Perillae Semen extract, the mixed extract includes: a mixed extract of two kinds of herbal medicines, such as a mixed extract of Brassicae Semen and Adenophorae Radix, a mixed extract of Brassicae Semen and Lonicerae Folium, a mixed extract of Brassicae Semen and Perillae Semen, a mixed extract of Adenophorae Radix and Lonicerae Folium, a mixed extract of Adenophorae Radix and Perillae Semen, and a mixed extract of Lonicerae Folium and Perillae Semen; a mixed extract of three kinds of herbal medicines, such as a mixed extract of Brassicae Semen, Adenophorae Radix, and Lonicerae Folium, a mixed extract of Brassicae Semen, Adenophorae Radix, and Perillae Semen, a mixed extract of Brassicae Semen, Lonicerae Folium, and Perillae Semen, and a mixed extract of Adenophorae Radix, Lonicerae Folium, and Perillae Semen; and a mixed extract of four kinds of herbal medicines, such as a mixed extract of Brassicae Semen, Adenophorae Radix, Lonicerae Folium, and Perillae Semen.

Herein, Brassicae Semen is also called a mustard seed, and refers to a well-ripened seed of *Brassica juncea* Czern. et Cosson or a variety thereof (Cruciferae). *Donguibogam* describes that Brassicae Semen treats swelling or paralysis caused by wind toxin, blood stasis due to being bumped or hit, pain in the back, cold kidney, and heart pain.

Herein, Adenophorae Radix is a root of *Adenophora triphylla* var. *japonica* Hara or *Adenophora stricta* Miq. (Campanulaceae). This medicine is a conical-cylindrical, slightly bent root that is 7-27 cm in length and 8-30 mm in diameter. The outer surface is yellowish white or light yellowish, and rough skins may remain in the hollow portion. Many deeply transverse lines are formed on the head of the root, and these lines have a round ring shape but are discontinuous. Vertical patterns and vertical grooves are formed at the bottom of the root. The texture of the root is light, sparse, and easily bent. The bent surface is not flat, yellowish-white, and has many cracks. This medicine slightly smells and tastes slightly sweet.

Herein, Lonicerae Folium is also called Lonicerae Caulis. This medicine corresponds to leaves and vine stems of *Lonicera japonica* Thunberg (Caprifoliaceae). Known effects thereof are clearing heat and relieving toxicity, antibacterial, antiviral, and antifungal effects, astriction, promoting urination, suppressing cholesterol absorption, and the like.

Herein, Perillae Semen is also called *Perilla sikokiana* Nakai. This medicine is a fruit of *Perilla frutescens* L. Britton var. acuta (Thunb.) Kudo or *Perilla frutescens* Britton var. crispa Decne (Labiatae). This medicine is a fruit, close to an ovate or sphere shape, and 0.6-2 mm in diameter. The outer surface is grayish brown or dark grayish brown and has a slightly protuberant net pattern. The lower part is slightly pointed and has a white dot-patterned fruit tip mark. The fruit peel is thin, and easily broken when pressed. The seed bark is membrane and the cotyledons are rich in oil. This medicine has almost no smell, but is known to have a peculiar scent when chewed and have a rough and slightly spicy taste.

The Brassicae Semen, Adenophorae Radix, Lonicerae Folium, and Perillae Semen extracts used in the present disclosure may be purchased, or obtained by direct extraction from the herbal medicines. The extraction may be performed after the respective herbal medicines are cut or pulverized into proper sizes.

In a case where the extracts used in a composition of the present disclosure are obtained by direct extraction from the herbal medicines Brassicae Semen, Adenophorae Radix, Lonicerae Folium, and Perillae Semen, various extraction solvents, such as polar solvents or non-polar solvents, may be used.

Suitable polar solvents may include (i) water, (ii) a C1 to C6 lower alcohol (specifically, methanol, ethanol, propanol, butanol, n-propanol, iso-propanol, n-butanol, 1-pentanol, 2-butoxyethanol, or ethylene glycol), (iii) acetic acid, (iv) dimethyl-formamide (DMFO), and (v) dimethyl sulfoxide (DMSO). Suitable non-polar solvents include acetone, acetonitrile, ethyl acetate, methyl acetate, fluoroalkanes, pentane, hexane, 2,2,4-trimethylpentane, decane, cyclohexane, cyclopentane, diisobutylene, 1-pentene, 1-chlorobutane, 1-chloropentane, o-xylene, diisopropylether, 2-chloropropane, toluene, 1-chloropropane, chlorobenzene, benzene, diethyl ether, diethyl sulfide, chloroform, dichloromethane, 1,2-dichloroethane, aniline, diethyl amine, ether, carbon tetrachloride, and tetrahydrofuran (THF).

The amount of the extraction solvent may vary depending on the amounts of Brassicae Semen, Adenophorae Radix, Lonicerae Folium, and Perillae Semen to be subjected to extraction, and specifically, an extraction solvent having a volume 1-20 times, specifically, 5-15 times, more specifically, 5-12 times, or 7-12 times the weight of Brassicae Semen, Adenophorae Radix, Lonicerae Folium, Perillae Semen, or a mixture thereof may be used. Most specifically, an extraction solvent having a volume 10 times the weight of Brassicae Semen, Adenophorae Radix, Lonicerae Folium, Perillae Semen, or a mixture thereof may be used.

The extraction temperature of the extracts of the present disclosure is not particularly limited, and the extraction temperature may be for example 0-120° C., and specifically, 15-95° C. In an embodiment of the present disclosure, the extraction temperature is room temperature.

The extraction time for the extracts of the present disclosure is not particularly limited, and the extraction time may be for example 1 hour to 10 days, specifically, 1-144 hours, 1-120 hours, 1-96 hours, 1-72 hours, 1-48 hours, 1-36 hours, 1-24 hours, 1-12 hours, 1-10 hours, or 1-6 hours. The extraction time may be more specifically 3-144 hours, 3-120 hours, 3-96 hours, 3-72 hours, 3-48 hours, 3-36 hours, 3-24 hours, 3-12 hours, 3-10 hours, 5-144 hours, 5-120 hours, 5-96 hours, 5-72 hours, 5-48 hours, 5-36 hours, 5-24 hours, 5-12 hours, 5-10 hours, 8-96 hours, 8-72 hours, 8-48 hours, 8-36 hours, 8-24 hours, 8-12 hours, 8-10 hours, 12-120 hours, 12-96 hours, 12-72 hours, 12-48 hours, 12-36 hours, 12-24 hours, 24-120 hours, 24-96 hours, 24-72 hours, 24-48 hours, 36-96 hours, 36-72 hours, 36-48 hours, 48-96 hours, 48-84 hours, 60-96 hours, 60-84 hours, or 60-72 hours, and most specifically 72 hours.

The extracts of the present disclosure may be extracted by a known natural substance extraction method. For example, the extraction may be carried out by cold extraction, hot-water extraction, ultrasonic extraction, reflux cooling extraction, or heating extraction, and specifically, cold extraction. The extraction may be repeated one to ten times, and more specifically two to seven times.

According to an embodiment of the present disclosure, the Brassicae Semen, Adenophorae Radix, Lonicerae Folium, and Perillae Semen extracts used in the present disclosure can be extracted with an organic solvent, water, or a mixed solvent thereof. Examples of the organic solvent are a C1 to C6 lower alcohol, petroleum ether, hexane, benzene, chloroform, methylene chloride, ether, ethyl acetate, and acetone. According to another specific embodiment of the present disclosure, the organic solvent of the present disclosure is a mixed solvent of ethyl alcohol and water.

The concentration of the organic solvents, such as a C1 to C6 lower alcohol, petroleum ether, hexane, benzene, chloroform, methylene chloride, ether, ethyl acetate, and acetone, may be 1-100% (v/v), specifically 10-100% (w/w), 20-100% (w/w), 30-100% (w/w), 40-100% (w/w), 50-100% (w/w), 60-100% (w/w), 70-100% (w/w), or 80-100% (w/w), and more specifically 10-95% (w/w), 10-80% (w/w), 10-70% (w/w), 10-60% (w/w), 10-50% (w/w), 10-40% (w/w), or 10-30% (w/w), still more specifically 20-80% (w/w), 20-70% (w/w), 20-60% (w/w), 20-50% (w/w), 20-40% (w/w), or 20-30% (w/w), and most specifically 25% (w/w), but is not limited thereto.

According to still another embodiment of the present disclosure, the Brassicae Semen, Adenophorae Radix, Lonicerae Folium, and Perillae Semen extracts of the present disclosure may be extracted with the above-described water, a C1 to C6 lower alcohol, or a mixed solvent thereof, or may be, after extraction and concentration (under reduced pressure), further extracted or fractionated with an organic solvent selected from the group consisting of petroleum ether, hexane, benzene, chloroform, methylene chloride, ether, ethyl acetate, and acetone as described above.

Meanwhile, the mixed extract of the Brassicae Semen, Adenophorae Radix, Lonicerae Folium, and Perillae Semen extracts used in the present disclosure may be prepared by mixing individual Brassicae Semen, Adenophorae Radix, Lonicerae Folium, and Perillae Semen extracts, or may be prepared by treating a mixture of two or more herbal medicines selected from Brassicae Semen, Adenophorae Radix, Lonicerae Folium, and Perillae Semen with an extraction solvent.

In the present disclosure, the Brassicae Semen, Adenophorae Radix, Lonicerae Folium, and Perillae Semen extracts may be used in the form of a crude extract extracted by a solvent, and may be used through high-purity purification.

As used herein, the term "extract" has a meaning that is commonly used as a crude extract in the art as described above, and broadly, encompasses a fraction obtained by additionally fractionating the extract. In other words, the Brassicae Semen, Adenophorae Radix, Lonicerae Folium, and Perillae Semen extracts include not only ones obtained by using the above-described extraction solvents but also ones obtained by additionally applying a purification procedure to the same. For example, the Brassicae Semen, Adenophorae Radix, Lonicerae Folium, and Perillae Semen extracts of the present disclosure include fractions obtained through various purification methods that are additionally performed, such as a fraction obtained by passing the extracts through an ultrafiltration membrane with a predetermined molecular weight cut-off value and a fraction obtained by various types of chromatography (manufactured for separation depending on size, charge, hydrophobicity, or hydrophilicity). The Brassicae Semen, Adenophorae Radix, Lonicerae Folium, and Perillae Semen extracts used in the present disclosure may be prepared in a powder type by additional procedures, such as distillation under reduced pressure and freeze-drying or spray drying.

According to a specific embodiment of the present disclosure, Brassicae Semen, Adenophorae Radix, Lonicerae Folium, Perillae Semen, or a mixture thereof is washed and dried, and then mixed at a predetermined weight ratio. Thereafter, the mixture is placed in an extraction solvent having a volume (ml) 1-20 times the weight (g) thereof, and then subjected to extraction while well stirred at 15-95° C. for 1-144 hours. Then, the extract was filtered, concentrated under reduced pressure at 50-65° C., and then freeze-dried, thereby obtaining a powder-type complex herbal medicine extract (mixed extract).

According to another embodiment of the present disclosure, Brassicae Semen, Adenophorae Radix, Lonicerae Folium, and Perillae Semen, or a mixture thereof is added to an extraction solvent having a volume (ml) 1-20 times the weight (g) thereof, and then subjected to extraction while well stirred at 15-95° C. for 1-144 hours. Then, each extract is filtered, concentrated under reduced pressure at 50-65° C., and freeze-dried, thereby obtaining a powder-type herbal medicine extract. Thereafter, the respective herbal medicine extracts are mixed at a predetermined weight ratio, thereby obtaining a powder-type complex herbal medicine extract (mixed extract).

According to a particular embodiment of the present disclosure, Brassicae Semen, Adenophorae Radix, Lonicerae Folium, and Perillae Semen are mixed at a weight ratio of 1:1:1:1, and then an ethanol aqueous solution having a volume 10 times the weight is added thereto, followed by extraction at room temperature for 72 hours. The extract is concentrated under reduced pressure at 50-65° C., and then the concentrate is freeze-dried, thereby obtaining a complex herbal medicine extract of Brassicae Semen, Adenophorae Radix, Lonicerae Folium, and Perillae Semen.

According to another particular embodiment of the present disclosure, Brassicae Semen, Adenophorae Radix, and Lonicerae Folium are mixed at a weight ratio of 1:1:1, and then an ethanol aqueous solution having a volume 10 times the weight is added thereto, followed by extraction at room temperature for 72 hours. The extract is concentrated under reduced pressure at 50-65° C., and then the concentrate is freeze-dried, thereby obtaining a complex herbal medicine extract of Brassicae Semen, Adenophorae Radix, and Lonicerae Folium.

The mixed extract of four kinds, Brassicae Semen, Adenophorae Radix, Lonicerae Folium, and Perillae Semen used in the present disclosure may contain herbal medicine extracts of Brassicae Semen, Adenophorae Radix, Lonicerae Folium, and Perillae Semen at a mixing weight ratio of 1-10:1-10:1-10:1-10, 1:1-10:1-10:1-10, 1-10:1:1-10:1-10, 1-10:1-10:1:1-10, 1-10:1-10:1-10:1, 1:1:1-10:1-10, 1:1-10:1:1-10, 1:1-10:1-10:1, 1-10:1:1:1-10, 1-10:1:1-10:1, 1-10:1-10:1:1, 1:1:1:1-10, 1:1:1-10:1, 1:1-10:1:1, or 1-10:1:1:1, at a mixing weight ratio of 1-5:1-5:1-5:1-5, 1:1-5:1-5:1-5, 1-5:1:1-5:1-5, 1-5:1-5:1:1-5, 1-5:1-5:1-5:1, 1:1:1-5:1-5, 1:1-5:1-5:1, 1:1-5:1:1-5, 1-5:1:1-5:1, 1-5:1:1:1-5, 1-5:1-5:1:1, 1:1:1:1-5, 1:1:1-5:1, 1:1-5:1:1, or 1-5:1:1:1, at a mixing weight ratio of 1-4:1-4:1-4:1-4, 1:1-4:1-4:1-4, 1-4:1:1-4:1-4, 1-4:1-4:1:1-4, 1-4:1-4:1-4:1, 1:1:1-4:1-4, 1:1-4:1:1-4, 1:1-4:1-4:1, 1-4:1:1-4:1, 1-4:1:1:1-4, 1-4:1-4:1:1, 1:1:1:1-4, 1:1:1-4:1, 1:1-4:1:1, or 1-4:1:1:1, or at a mixing weight ratio of 1-3:1-3:1-3:1-3, 1:1-3:1-3:1-3, 1-3:1:1-3:1-3, 1-3:1-3:1:1-3, 1-3:1-3:1-3:1, 1:1:1-3:1-3, 1:1-3:1-3:1, 1:1-3:1:1-3, 1-3:1:1-3:1, 1-3:1:1:1-3, 1-3:1-3:1:1, 1:1:1:1-3, 1:1:1-3:1, 1:1-3:1:1, 1-3:1:1:1, or 1:1:1:1.

The mixed extract of three kinds, Brassicae Semen, Adenophorae Radix, and Lonicerae Folium used in the present disclosure may contain Brassicae Semen, Adenophorae Radix, and Lonicerae Folium herbal medicine extracts at a mixing weight ratio of 1-10:1-10:1-10, 1:1-10:1-10, 1-10:1:1-10, 1-10:1-10:1, 1:1:1-10, 1:1-10:1, or 1-10:1:1, at a mixing weight ratio of 1-5:1-5:1-5, 1:1-5:1-5, 1-5:1:1-5, 1-5:1-5:1, 1:1:1-5, 1:1-5:1, or 1-5:1:1, at a mixing weight ratio of 1-4:1-4:1-4, 1:1-4:1-4, 1-4:1:1-4, 1-4:1-4:1, 1:1:1-4, 1:1-4:1, or 1-4:1:1, or at a mixing weight ratio of 1-3:1-3:1-3, 1:1-3:1-3, 1-3:1:1-3,1-3:1-3:1, 1:1:1-3,1:1-3:1, 1-3:1:1, or 1:1:1.

In a more specific embodiment of the present disclosure, the mixing weight ratio of the Brassicae Semen, Adenophorae Radix, and Lonicerae Folium herbal medicine extracts may be 1:1:1, 1:1:2, 1:1:4, 1:2:1, 1:4:1, 2:1:1, or 4:1:1, but is not limited thereto.

As used herein, the term "mixing weight ratio" refers to a weight ratio (w/w) of respective components before an extraction process or a weight ratio (w/w) of respective extracts.

When the "mixed weight ratio" is expressed by the weight ratio (w/w) of respective extracts, the mixing weight ratio is calculated by a weight ratio of individual extracts mixed to prepare a mixed extract. However, when the "mixing weight ratio" means a weight ratio (w/w) of respective components before an extraction process, the mixing weight ratio is calculated differently depending on whether the extraction process is carried out before or after the mixing of the respective components. For example, when the complex extract of the present disclosure is prepared through a single extraction process in which the mixture of Brassicae Semen, Adenophorae Radix, and Lonicerae Folium is subjected to extraction with an extraction solvent, the "mixing weight ratio" refers to a weight ratio of the respective single components, Brassicae Semen, Adenophorae Radix, and Lonicerae Folium contained in the mixture. In addition, when the complex extract of the present disclosure is prepared in a manner in which the extracts of the single components Brassicae Semen, Adenophorae Radix, and Lonicerae Folium are separately prepared and then the extracts of the two components thereof are mixed, the "mixing weight ratio" refers to a weight ratio of "single component-based weights", each of which is calculated by the following equation.

[Equation]

Single component-based weight=weight of single component used in preparation of single extract×(weight of single extract used in preparation of final complex extract/weight of prepared single extract)

As used herein, the term "to" or "-" between two numerical values refers to an interval between the numerical values including numerical values described before and after the term.

The composition of the present disclosure may be prepared into a pharmaceutical composition.

According to a specific embodiment of the present disclosure, the composition of the present disclosure is a pharmaceutical composition including: (a) as an active ingredient, a mixed extract of two or more selected from the group consisting of a Brassicae Semen extract, an Adenophorae Radix extract, a Lonicerae Folium extract, and a Perillae Semen extract; and (b) a pharmaceutically acceptable carrier.

As used herein, the term "pharmaceutical effective amount" refers to an amount sufficient to attain efficacy of the above-described mixed extract of Brassicae Semen, Adenophorae Radix, Lonicerae Folium, and Perillae Semen to treat or prevent a respiratory disease. The present disclosure is directed to a composition comprising extracts extracted from the natural plant materials, Brassicae Semen, Adenophorae Radix, Lonicerae Folium, and Perillae Semen, and even the administration of an excess of the composition causes no side effects in the human body, and thus a person skilled in the art could select and implement the upper limit of the amount of the extracts contained in the composition of the present disclosure within an appropriately range.

As used herein, the term "respiratory disease" includes a respiratory disease selected from the group consisting of a cold, rhinitis, pharyngitis, laryngitis, pharyngolaryngitis, pneumonia, acute or chronic bronchitis, asthma, and chronic obstructive pulmonary disease, but is not limited thereto.

As used herein, the term "treatment" refers to a reduction, suppression, amelioration, or eradication of a respiratory disease, which is a target disease of the present disclosure. As used herein, the term "prevention" refers to all the acts that inhibit or delay the occurrence of a respiratory disease, which is a target disease of the present disclosure, and encompasses a therapeutic meaning.

As validated in the following examples, the administration of the complex extract (mixed extract) of herbal medicines selected from the group consisting of Brassicae Semen, Adenophorae Radix, Lonicerae Folium, and Perillae Semen of the present disclosure shows an effect of significantly reducing lung tissue damage in emphysema mouse models.

In addition, the complex herbal medicine extract of the present disclosure significantly inhibits the aging of pulmonary epithelial cell lines, induced by fine dust, and dose-dependently increases the expression degree of telomerase that extends the length of telomeres.

In addition, the complex herbal medicine extract of the present disclosure shows an excellent anti-inflammatory effect by inhibiting NO production and the expression of anti-inflammatory factors (IL-6, IL-1$\beta$, and iNOS) of mouse macrophage cell lines treated with LPS and an excellent antioxidative effect by increasing the expression of an antioxidative factor (HO-1).

In addition, the complex herbal medicine extract of the present disclosure shows an excellent anti-inflammatory effect by inhibiting the expression of anti-inflammatory factors (IL-6, IL-1$\beta$, and iNOS) in the mouse macrophage cell lines treated with LPS, under various mixing ratio conditions, and an excellent antioxidative effect by increasing the expression of an antioxidative factor (HO-1).

In addition, the complex herbal medicine extract of the present disclosure shows an excellent anti-inflammatory effect by inhibiting the expression of anti-inflammatory factors (IL-6 and iNOS) even when the extract is extracted by hot-water extraction and an extraction solvent (ethanol) with various concentrations and an excellent antioxidative effect by increasing the expression of the antioxidative factor HO-1.

As well, the complex herbal medicine extract of the present disclosure, compared with a single herbal medicine extract, significantly inhibits the expression of inflammatory factors (IL-6, IL-1$\beta$, and TNF-$\alpha$) in the lung tissue of the pulmonary inflammation models induced by LPS, thereby showing a synergistic effect in an anti-inflammatory effect compared with a single herbal medicine extract.

The above results of the examples indicate that the composition comprising the complex herbal medicine extract of the present disclosure can be used in the prevention, alleviation, or treatment of a respiratory disease, such as pneumonia, bronchitis, chronic obstructive pulmonary disease, or asthma, caused by inflammation and aging, and can be used as an alternative for a conventional respiratory disease medicine.

Especially, not only a mixed extract of four kinds, Brassicae Semen, Adenophorae Radix, Lonicerae Folium, and Perillae Semen of the present disclosure but also a mixed extract of three kinds, Brassicae Semen, Adenophorae Radix, and Lonicerae Folium, except for Perillae Semen, shows an effect of treating a respiratory disease.

In cases where the composition of the present disclosure is prepared into a pharmaceutical composition, the pharmaceutical composition of the present disclosure may contain a pharmaceutically acceptable carrier. The pharmaceutically acceptable carrier is normally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, and the like. The pharmaceutical composition of the present disclosure may further contain, in addition to the above ingredients, a lubricant, a humectant, a sweetener, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present disclosure may be administered orally or parenterally, and examples of parenteral administration may include intravenous administration, subcutaneous administration, intradermal administration, intramuscular administration, intranasal administration, mucosal administration, intradural administration, intraperitoneal administration, intraocular administration, and the like, and specifically, the pharmaceutical composition of the present disclosure may be administered orally.

The suitable dose of the pharmaceutical composition of the present disclosure varies depending on factors, such as a formulating method, a manner of administration, patient's age, body weight, gender, morbidity, and food, a time of administration, a route of administration, an excretion rate, and response sensitivity. The ordinarily skilled practitioners can easily determine and prescribe the dose that is effective for the desired treatment or prevention. According to a specific embodiment of the present disclosure, the daily dose of the pharmaceutical composition of the present disclosure is 0.001-1,000 mg/kg. The daily dose of the pharmaceutical composition of the present disclosure may be for example 0.1-1000 mg/kg, 0.1-900 mg/kg, 0.1-800 mg/kg, 0.1-700 mg/kg, 0.1-600 mg/kg, 0.1-500 mg/kg, 0.1-400 mg/kg, 0.1-300 mg/kg, 0.1-200 mg/kg, 0.1-100 mg/kg, 0.1-50 mg/kg, 0.1-30 mg/kg, 0.1-20 mg/kg, 0.1-10 mg/kg, 0.1-7 mg/kg, or 0.1-5 mg/kg, and may be 1-1000 mg/kg, 1-900 mg/kg, 1-800 mg/kg, 1-700 mg/kg, 1-600 mg/kg, 1-500 mg/kg, 1-400 mg/kg, 1-300 mg/kg, 1-200 mg/kg, 1-100 mg/kg, 1-50 mg/kg, 1-30 mg/kg, 1-20 mg/kg, 1-10 mg/kg, 1-7 mg/kg, or 1-5 mg/kg, and more specifically may be 1, 2, 3, 4, 5, 6, 7, 8, 9, or 10 mg/kg. In another embodiment, the daily dose of the pharmaceutical composition of the present disclosure may be for example 100-900 mg/kg, 100-800 mg/kg , 100-700 mg/kg , 100-600 mg/kg, 100-500 mg/kg, 100-400 mg/kg, 100-300 mg/kg, or 100-200 mg/kg, may be 200-900 mg/kg, 200-800 mg/kg, 200-700 mg/kg, 200-600 mg/kg, 200-500 mg/kg, 200-400 mg/kg, or 200-300 mg/kg, may be 300-900 mg/kg, 300-800 mg/kg, 300-700 mg/kg , 300-600 mg/kg, 300-500 mg/kg, or 300-400 mg/kg, and may be 400-900 mg/kg, 400-800 mg/kg , 400-700 mg/kg , 400-600 mg/kg, or 400-500 mg/kg, and more specifically, 100 mg/kg, 200 mg/kg, 300 mg/kg, 400 mg/kg, 500 mg/kg, 600 mg/kg, 700 mg/kg, 800 mg/kg, 900 mg/kg, or 1000 mg/kg, but is not limited thereto.

The pharmaceutical composition of the present disclosure may be formulated into a unit dosage form or may be prepared in a multi-dose container by using a pharmaceutically acceptable carrier and/or excipient according to a method that can be easily implemented by a person having an ordinary skill in the art to which the present disclosure pertains. The formulation may be a solution in an oily or aqueous medium, a suspension, an emulsion, an extract, a powder, granules, a tablet, or a capsule, and may further contain a dispersant or a stabilizer.

The pharmaceutical composition of the present disclosure may be administered in combination with a known compound or pharmaceutical composition having effects of preventing and treating a respiratory disease or respiratory disease-related symptoms.

In accordance with another aspect of the present disclosure, there is provided a food composition for prevention or alleviation of a respiratory disease, the food composition comprising, as an active ingredient, a mixed extract of two or more selected from the group consisting of a Brassicae Semen extract, an Adenophorae Radix extract, a Lonicerae Folium extract, and a Perillae Semen extract. The food composition may be used as a health functional food or may be added to various types of foods.

As used herein, the term "alleviation" refers to all the acts that reduce symptoms of a respiratory disease, which is a target disease of the present disclosure.

The present disclosure also provides a health functional food containing the food composition. The health functional food may be drinks, meats, chocolates, foods, confectionery, pizzas, instant noodles, other noodles, gums, ice creams, alcohol drinks, vitamin complexes, and health supplement foods.

The content of the mixed extract of the present disclosure contained in the food composition may be appropriately controlled according to the form of food, the desired use, or the like, and is not particularly limited thereto. For example, the content of the mixed extract may be 0.001-30 wt % or 0.01-20 wt % of the entire food weight, and the health food composition may be 0.001-15 g, 0.02-10 g, or 0.3-1 g on the basis of 100 ml thereof, but is not limited thereto.

The composition comprising a mixed extract of Brassicae Semen, Adenophorae Radix, Lonicerae Folium, and Perillae Semen of the present disclosure, when prepared into a food composition, may contain ingredients that are ordinarily added in the manufacture of foods as well as the extract as an active ingredient. The added ingredients include, for example, a protein, a carbohydrate, a fat, a nutrient, a seasoning, and a flavoring agent. Examples of the foregoing carbohydrate may include typical sugars (monosaccharides, such as glucose and fructose; disaccharides, such as maltose, sucrose, and oligosaccharides; and polysaccharides, such as dextrin and cyclodextrin) and sugar alcohols, such as xylitol, sorbitol, and erythritol. Examples of the flavoring agent may include natural flavoring agents (thaumatin, and stevia extract (e.g., rebaudioside A, glycyrrhizin, etc.)) and synthetic flavoring agents (saccharin, aspartame, etc.). For example, the food composition of the present disclosure, when is prepared into a drink, may further contain citric acid, liquefied fructose, sugar, glucose, acetic acid, malic acid, fruit juice, an *Eucommia ulmoides* extract, a jujube extract, and a licorice extract, in addition to the extract of the present disclosure.

Since the food composition for prevention or alleviation of a respiratory disease of the present disclosure contains, as an active ingredient, a mixed extract of Brassicae Semen, Adenophorae Radix, Lonicerae Folium, and Perillae Semen, in the same manner as "the pharmaceutical composition for prevention or treatment of a respiratory disease", a description of overlapping contents therebetween is omitted to avoid excessive redundancy of the present specification.

Furthermore, according to still another aspect of the present disclosure, the present disclosure provides a method for prevention or treatment of a respiratory disease, the method including administering to a subject the above-described pharmaceutical composition comprising as an active ingredient a mixed extract of two or more selected from the group consisting of a Brassicae Semen extract, an Adenophorae Radix extract, a Lonicerae Folium extract, and a Perillae Semen extract of the present disclosure.

Furthermore, according to another aspect of the present disclosure, the present disclosure provides a method for prevention or alleviation of a respiratory disease, the method including administering to a subject the above-described food composition comprising as an active ingredient a mixed extract of two or more selected from the group consisting of a Brassicae Semen extract, an Adenophorae Radix extract, a Lonicerae Folium extract, and a Perillae Semen extract.

The respiratory disease, which is the target disease of the treatment method or alleviation method of the present disclosure, is the same as defined in relation to the respiratory disease, which is the target disease to be treated with the pharmaceutical composition.

As used herein, the term "administration" or "administer" refers to the direct administration of a therapeutically effective amount of the composition of the present disclosure to a subject (i.e., an object) undergoing a respiratory disease, thereby forming the same amount thereof in the body of the subject.

The term "therapeutically effective amount" of the composition refers to the content of the composition, which is sufficient to provide a therapeutic or preventive effect to a subject to which composition is administered, and thus the term has a meaning encompassing "prophylactically effective amount." As used herein, the term "subject" is a mammal including a human, a mouse, a rat, a guinea pig, a dog, a cat, a horse, a cow, a pig, a monkey, a chimpanzee, a baboon, or a rhesus monkey. Most specifically, the subject of the present disclosure is a human.

Since the method for prevention or treatment of a respiratory disease of the present disclosure includes administering the pharmaceutical composition for prevention or treatment or the food composition for prevention or alleviation of a respiratory disease according to an aspect of the present disclosure, a description of overlapping contents therebetween is omitted to avoid excessive redundancy of the present specification.

Advantageous Effects

Features and advantages of the present disclosure are summarized as follows.

(a) The present disclosure is directed to a pharmaceutical composition for prevention or treatment of a respiratory disease and a food composition for prevention or alleviation of a respiratory disease, each of the compositions containing a mixed extract of two or more selected from the group consisting of a Brassicae Semen extract, an Adenophorae Radix extract, a Lonicerae Folium extract, and a Perillae Semen extract.

(b) The composition comprising a mixed extract of Brassicae Semen, Adenophorae Radix, Lonicerae Folium, and Perillae Semen of the present disclosure has effects of preventing a respiratory disease and relieving symptoms thereof, restore lung tissue damage, inhibits inflammation and aging induced by an inflammation-induction substance, such as fine dust, and has an excellent antioxidative effect. Especially, the composition of the present disclosure is expected to be able to fundamentally treat a degenerative respiratory disease induced by fine dust, unlike a conventional symptom reliever, by increasing the expression of telomerase that extends the length of telomeres.

DETAILED DESCRIPTION

Figure 1:
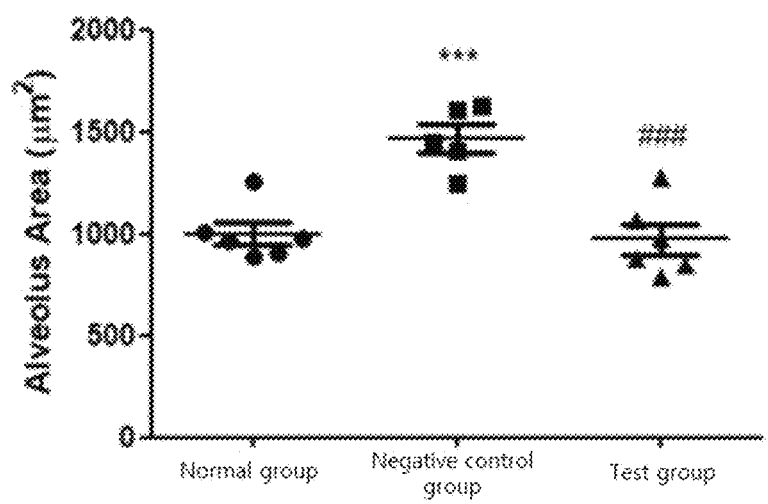
FIG. 1 shows the results of observing lung tissues of PPE-induced emphysema mouse models and the alveolar surface area in each lung tissue, in order to investigate the lung tissue damage inhibitory effect of the complex extract of four kinds of herbal medicines in Preparative Example 1 of the present disclosure.

Hereinafter, the present disclosure will be described in more detail with reference to examples. These examples are only for illustrating the present disclosure more specifically, and it would be apparent to those skilled in the art that the scope of the present disclosure is not limited by these examples according to the gist of the present disclosure.

EXAMPLES

Throughout the present specification, the "%" used to express the concentration of a specific material, unless

Preparative Examples

Preparative Example 1: Preparation of Complex Extract (Mixed Extract) of Four Kinds of Herbal Medicines Washed and dried Brassicae Semen, Adenophorae Radix, Lonicerae Folium, and Perillae Semen were used in tests. The herbal medicines Brassicae Semen, Adenophorae Radix, Lonicerae Folium, and Perillae Semen were mixed at a weight ratio of 1:1:1:1 to a total of 60 g, and 25% (v/v) ethanol aqueous solution having a volume 10 times the weight was added thereto, followed by extraction while well stirring at room temperature for 72 hours. The extract was filtered, concentrated under reduced pressure at 50-65° C., and then freeze-dried, thereby obtaining a powder-type complex extract (mixed extract) of herbal medicines. The yield was 12-13%.

Preparative Example 2: Preparation of Complex Extract (Mixed Extract) of Three Kinds of Herbal Medicines Washed and dried Brassicae Semen, Adenophorae Radix, and Lonicerae Folium were used in tests. The herbal medicines Brassicae Semen, Adenophorae Radix, and Lonicerae Folium were mixed at a weight ratio of 1:1:1 to a total of 60 g, and 25% (v/v) ethanol aqueous solution having a volume 10 times the weight was added thereto, followed by extraction while well stirring at room temperature for 72 hours. The extract was filtered, concentrated under reduced pressure at 50-65° C., and then freeze-dried, thereby obtaining a powder-type complex extract (mixed extract) of herbal medicines. The yield was about 12-14%.

Preparative Example 3: Preparation of Complex Extracts (Mixed Extracts) of Three Kinds of Herbal Medicines According to Various Mixing Ratios Washed and dried Brassicae Semen, Adenophorae Radix, and Lonicerae Folium were used in tests. The herbal medicines Brassicae Semen, Adenophorae Radix, and Lonicerae Folium were mixed at weight ratios shown in Table 1 to a total of 30 g, and 25% (v/v) ethanol aqueous solution having a volume 10 times the weight was added thereto, followed by extraction while stirring at room temperature for 72 hours. Each of the extracts was filtered, concentrated under reduced pressure at 50-65° C., and then freeze-dried, thereby obtaining a total of seven types of complex herbal medicine extract powders. The yields thereof are shown in Table 1.

TABLE 1

| Classification | Brassicae Semen | Adenophorae Radix | Lonicerae Folium | Yield (%) |
| --- | --- | --- | --- | --- |
| Preparative Example 3-1 | 1 | 1 | 1 | 14.30 |
| Preparative Example 3-2 | 2 | 1 | 1 | 14.40 |
| Preparative Example 3-3 | 4 | 1 | 1 | 13.42 |
| Preparative Example 3-4 | 1 | 2 | 1 | 17.46 |
| Preparative Example 3-5 | 1 | 4 | 1 | 17.40 |
| Preparative Example 3-6 | 1 | 1 | 2 | 13.15 |
| Preparative Example 3-7 | 1 | 1 | 4 | 11.96 |

Preparative Example 4: Preparation of Complex Extracts (Mixed Extracts) of Three Kinds of Herbal Medicines According to Various Concentrations of Extraction Solvent (Ethanol)

Washed and dried Brassicae Semen, Adenophorae Radix, and Lonicerae Folium were used in tests. The herbal medicines Brassicae Semen, Adenophorae Radix, and Lonicerae Folium were mixed at the weight ratio (w/w) in Preparative Example 3-1 to a total of 30 g, and 25, 50, 70, and 90% ethanol aqueous solutions having a volume 10 times the weight were added thereto, followed by extraction while well stirring at room temperature for 72 hours. Each of the extracts was filtered, concentrated under reduced pressure at 50-65° C., and then freeze-dried, thereby obtaining a total of four types of complex herbal medicine extract powders. The yields thereof are shown in Table 2.

TABLE 2

| Classification | Ethanol aqueous solution concentration (%) | Yield (%) | Note |
| --- | --- | --- | --- |
| Preparative Example 4-1 | 25 | 14.38 | Same preparation method as in Preparative Example 3-1 |
| Preparative Example 4-2 | 50 | 14.22 | — |
| Preparative Example 4-3 | 70 | 11.76 | — |
| Preparative Example 4-4 | 90 | 8.23 | — |

Preparative Example 5: Preparation of Complex Herbal Medicine Extract (Mixed Extract) through Hot-Water Extraction Washed and dried Brassicae Semen, Adenophorae Radix, and Lonicerae Folium were used in tests. The herbal medicines Brassicae Semen, Adenophorae Radix, and Lonicerae Folium were mixed at the weight ratio (w/w) in Preparative Example 3-1 to a total of 30 g, and distilled water having a volume 10 times the weight was added thereto, followed by reflow extraction at a temperature of 90° C. for 3 hours. The extract was filtered, concentrated under reduced pressure at 50-65° C., and then freeze-dried, thereby obtaining a complex herbal medicine extract powder, and the yield thereof was about 15.38%.

Comparative Example 1: Preparation of Single-Herbal Medicine Extracts

Washed and dried Brassicae Semen, Adenophorae Radix, and Lonicerae Folium were used in tests. To 30 g of each of the herbal medicines Brassicae Semen, Adenophorae Radix, and Lonicerae Folium, 25% (v/v) ethanol aqueous solution having a volume 10 times the weight was added, followed by extraction while well stirring at room temperature for 72 hours. The extracts were filtered, concentrated under reduced pressure at 50-65° C., and then freeze-dried, thereby obtaining a total of three types of single herbal medicine extract powders. The yields thereof are shown in Table 3.

TABLE 3

| Classification | Kind of herbal medicine | Yield (%) |
| --- | --- | --- |
| Comparative Example 1-1 | Brassicae Semen | 11.21 |
| Comparative Example 1-2 | Adenophorae Radix | 17.71 |
| Comparative Example 1-3 | Lonicerae Folium | 10.56 |

Test Examples

Test Example 1: Lung Tissue Damage Inhibitory Effect of Complex Extract of Four Kinds of Herbal Medicines in PPE-Induced Emphysema Mouse Models In order to investigate a lung tissue damage inhibitory effect of the complex herbal medicine extract of the present disclosure prepared in Preparative Example 1, the following test was carried out.

After 7-week-old male C57BL/6 mice (Raonbio, Korea) were acclimated for at least one week, the animals were classified into (1) a normal group, (2) a group with emphysema induction and complex herbal medicine extract administration (test group), and (3) a group with emphysema induction and distilled water administration (negative control group). For the induction of emphysema in the test group and the negative control group, 0.25 U of porcine pancreatic elastase (PPE, Millipore, USA) was administered as a single drop into the mouse trachea. For the normal group, phosphate buffered saline (PBS) was administered as a single drop into the mouse trachea.

For the test group, the complex extract of four kinds of herbal medicines dissolved in distilled water was orally administered once/day at a dose of 200 mg/kg for three weeks from one week before PPE administration. For the normal group and the negative control group, only distilled water was orally administered. After the last administration of the complex extract of four kinds of herbal medicines or distilled water, the mice were anesthetized with carbon dioxide and the lung tissue was extracted. The extracted lung tissue was fixed in formalin and subjected to hematoxylin and eosin staining (H&E staining). The images taken by observing the lung tissue with an optical microscope (X100) are shown in FIG. 1.

As shown in FIG. 1, as a result of inducing emphysema by PPE, the alveolar dilation and lung tissue damage in the negative control group significantly increased by about 1.5 times compared with the normal group. In addition, the lung tissue damage was inhibited in the test group with administration of the complex extract of four kinds of herbal medicines compared with the emphysema induction group (negative control group).

It could be therefore verified that the complex extract of four kinds of herbal medicines of the present disclosure showed a lung tissue damage inhibitory effect in the emphysema mouse models.

Test Example 2: Anti-Aging Effect of Complex Extract of Four Kinds of Herbal Medicines on Fine Dust-Induced Cell Aging of Pulmonary Epithelial Cell Line In order to investigate an anti-aging effect of the complex herbal medicine extract of the present disclosure prepared in Preparative Example 1, the following test was carried out.

The human pulmonary endothelial cell line NCI-H292 cells (ATCC, USA) were incubated in the incubator of 5% $CO_2$ and 37° C. by using RPMI media (Corning, USA) containing 10% fetal bovine serum (FBS). The cells were prepared on a 96-well plate at $1 \times 10^4$ cells per well, and stabilized for 24 hours. After the cells were stabilized, the cell supernatant was removed, and then the cells were treated with the complex herbal medicine extract in Preparative Example 1 at 200 μg/ml, followed by incubation for 1 hour. Then, the cells were further treated with 50 μg/ml fine dust (particulate matter 10, PM10, NIST, USA) (test group). The normal group was treated with neither the complex herbal medicine extract nor fine dust, and the negative control group was treated with only fine dust. After five days, the cells were fixed in formalin, and then the degree of cell aging was investigated through senescence beta-galactosidase staining.

Figures 2, 3:
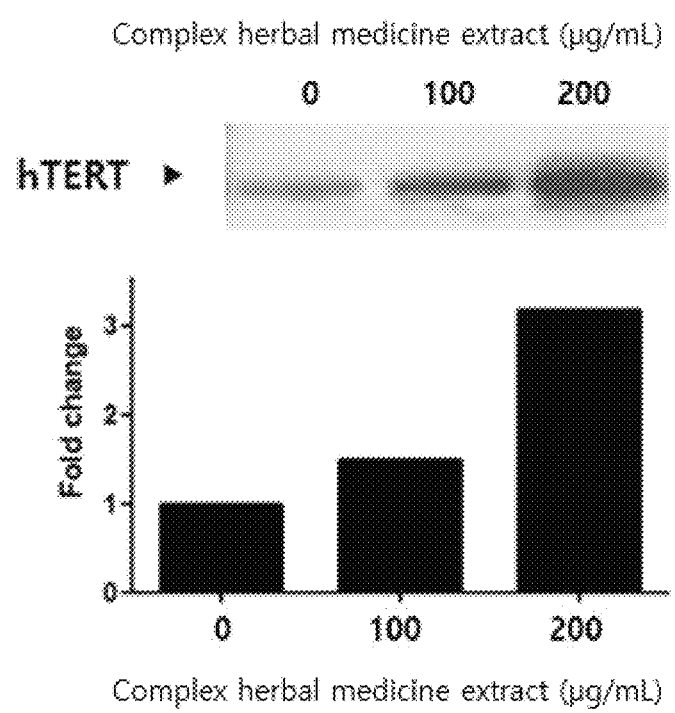
FIG. 2 shows the results of senescence beta-galactosidase staining after the treatment of pulmonary endothelial cell lines with fine dust, in order to investigate the anti-aging effect of the complex extract of four kinds of herbal medicines in Preparative Example 1 of the present disclosure.
FIG. 3 shows the western blot results of comparing the expression degrees of telomerase according to the concentrations (100 and 200 μg/ml) of the complex herbal medicine extract treating pulmonary endothelial cell line, in order to investigate the anti-aging effect of the complex extract of four kinds of herbal medicines in Preparative Example 1 of the present disclosure.

As shown in FIG. 2, cell aging caused by fine dust treatment was significantly reduced in the test group treated with the complex extract of four kinds of herbal medicines compared with the negative control group. It can be therefore seen that the complex extract of four kinds of herbal medicines of the present disclosure showed an excellent anti-aging effect.

Test Example 3: Telomerase Expression Increasing Effect of Complex Extract of Four Kinds of Herbal Medicines in Pulmonary Endothelial Cell Line (Anti-Aging Effect)

NCI-H292 cells were prepared on a 100 pi (φ) plate at $1 \times 10^6$ cells and stabilized. After 24 hours, the cells were treated with the complex herbal medicine extract in Preparative Example 1 at concentrations of 100 and 200 μg/ml. After 24 hours, the cells were collected and proteins were extracted, and then western blotting was performed using an antibody (ab32020, Abcam, USA) for human telomerase reverse transcriptase (hTERT), which is a catalytic small unit of telomerase.

As shown in FIG. 3, the pulmonary endothelial cell line was treated with the complex herbal medicine extract at concentrations of 100 and 200 μg/ml, and as a result, the expression of hTERT dose-dependently increased to 1.5 times and 3.2 times, respectively, compared with the non-treatment group (control group). It can be therefore seen that the complex extracts of four kinds of herbal medicines of the present disclosure showed an excellent anti-aging effect.

Test Example 4: Inhibitory Effect(Anti-Inflammatory Effect) of Complex Extract of Four Kinds of Herbal Medicines on LPS-Induced Nitric Oxide (NO) Production in Macrophage Cell Line The mouse macrophage cell line Raw 264.7 cells (ATCC, USA) were incubated in the incubator of 5% CO2 and 37° C. by using RPMI media (Invitrogen, USA) containing 10% fetal bovine serum (FBS). The cells were prepared on a 24-well plate at $2.5 \times 10^5$ cells per well, and stabilized. After 24 hours, the cell supernatant was removed, and then the cells were treated with the complex extract of four kinds of herbal medicines in Preparative Example 1 at concentrations of 0.5, 1, 2, and 4 mg/mL. After 1 hour, the cells were further treated with 100 ng/mL LPS. After 24 hours, the cell supernatant was collected and subjected to Griess test for measuring the change in NO production, and the concentration of NO was calculated using the standard curve according to the concentration of sodium nitrite ($NaNO_2$) (FIG. 4).

Figure 4:
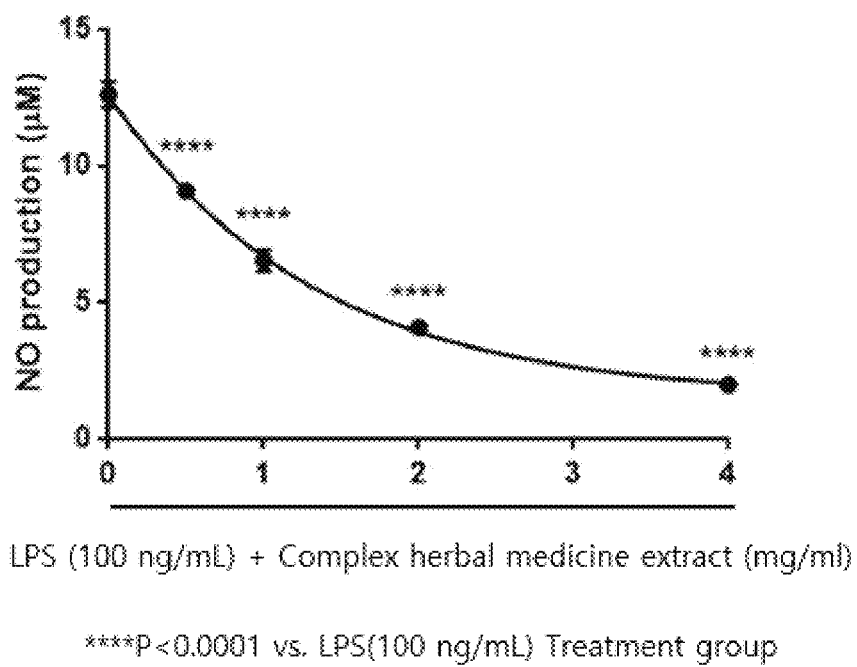
FIG. 4 is a graph showing the degree of nitric oxide (NO) production according to the treatment concentrations (0.5, 1, 2, 4 mg/ml) of the complex herbal medicine extract in mouse macrophage cell line treated with LPS, in order to investigate the anti-inflammatory effect of the complex extract of four kinds of herbal medicines in Preparative Example 1 of the present disclosure.

As shown in FIG. 4, the production of NO, which is an inflammatory factor, increased to a level of 12 μM by LPS treatment in macrophages (negative control group). In the test group treated with the complex herbal medicine extract at concentrations of 0.5, 1, 2, and 4 mg/ml together with LPS, the NO concentrations were 9.1, 6.5, 4.1, and 2 μM, respectively, showing a concentration-dependent reduction. It can be therefore seen that the complex extracts of four kinds of herbal medicines of the present disclosure showed an excellent anti-inflammatory effect.

Test Example 5: Lung Tissue Damage Inhibitory Effect of Complex Extract of Three Kinds of Herbal Medicines in Emphysema Mouse Models Induced by PPE In order to investigate a lung tissue damage inhibitory effect of the complex extract of three kinds of herbal medicines (Brassicae Semen, Adenophorae Radix, and Lonicerae Folium) of the present disclosure prepared in Preparative Example 2, the following test was carried out.

After 7-week-old male C57BL/6 mice (Raonbio, Korea) were acclimated for at least one week, the animals were classified into (1) a normal group, (2-4) groups with emphysema induction and complex herbal medicine extract (50, 100, 200 mg/kg) administration (test groups), and (3) a group with emphysema induction and distilled water administration (negative control group). For the induction of emphysema in the test groups and the negative control group, 1 unit of porcine pancreatic elastase (PPE, Millipore, USA) was administered as a single drop into the mouse trachea. For the normal group, phosphate buffered saline (PBS) was administered as a single drop into the mouse trachea.

For the test groups, the complex herbal medicine extracts dissolved in distilled water were orally administered once/day at doses of 50, 100, and 200 mg/kg, respectively, for three weeks from one week before PPE administration. For the normal group and the negative control group, only distilled water was orally administered. After the last administration of the complex herbal medicine extracts or distilled water, the mice were anesthetized with carbon dioxide and the lung tissue was extracted. The extracted lung tissue was fixed in formalin and subjected to hematoxylin and eosin staining (H&E staining). The images taken by observing the lung tissue with an optical microscope (X200) are shown in FIG. 5.

Figure 5:
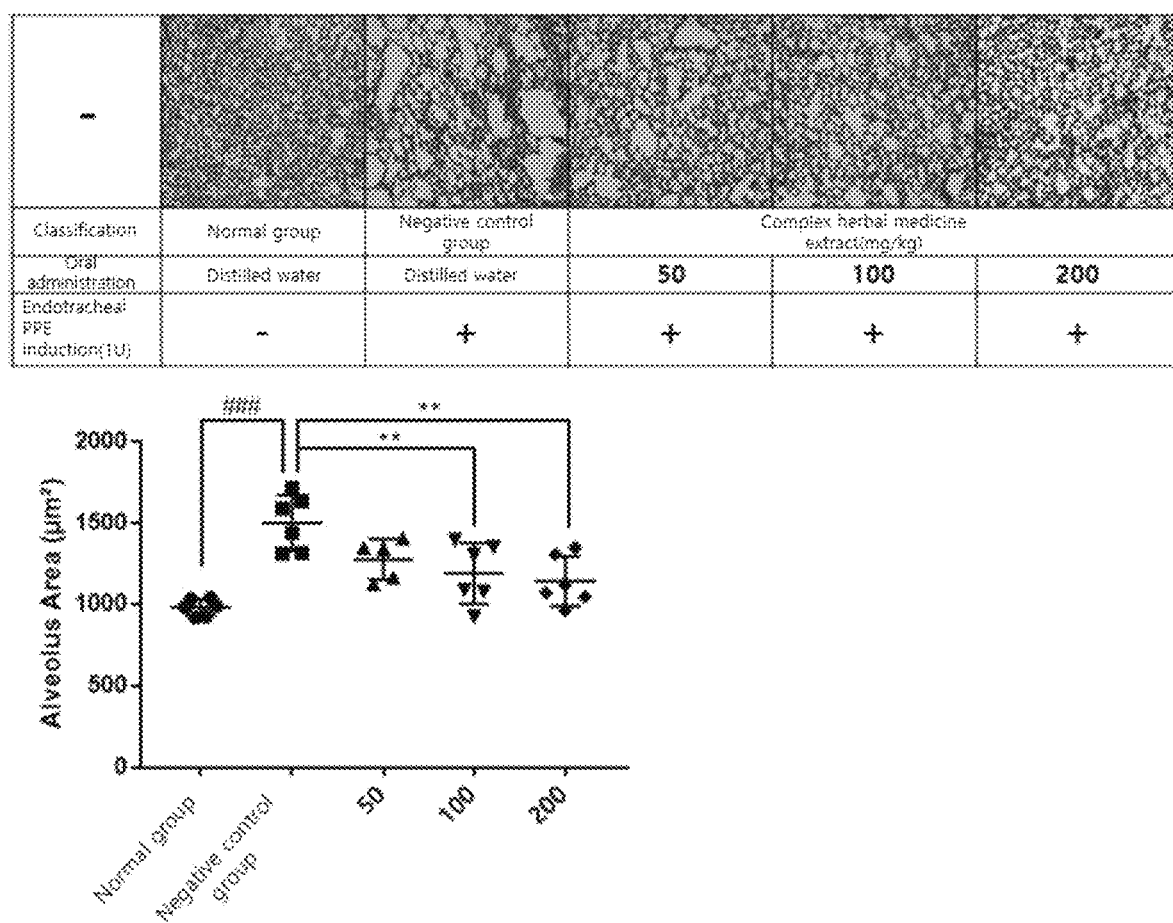
FIG. 5 shows the results of observing the lung tissue of PPE-induced emphysema mouse models by a microscope and the alveolar surface area in each lung tissue, in order to investigate the lung tissue damage inhibitory effect of the complex extract of three kinds of herbal medicines in Preparative Example 2 of the present disclosure.

As shown in FIG. 5, as a result of inducing emphysema with PPE, the alveolar dilation and lung tissue damage significantly increased by about 1.5 times in the negative control group compared with the normal group. In addition, the lung tissue damage was inhibited in a dose-dependent manner (50, 100, 200 mg/kg) in the test groups with administration of the complex extracts of three kinds of herbal medicines compared with the emphysema induction group (negative control group).

It could be therefore verified that the complex extracts of three kinds of herbal medicines of the present disclosure showed a lung tissue damage inhibitory effect in the emphysema mouse models.

Figure 6A:
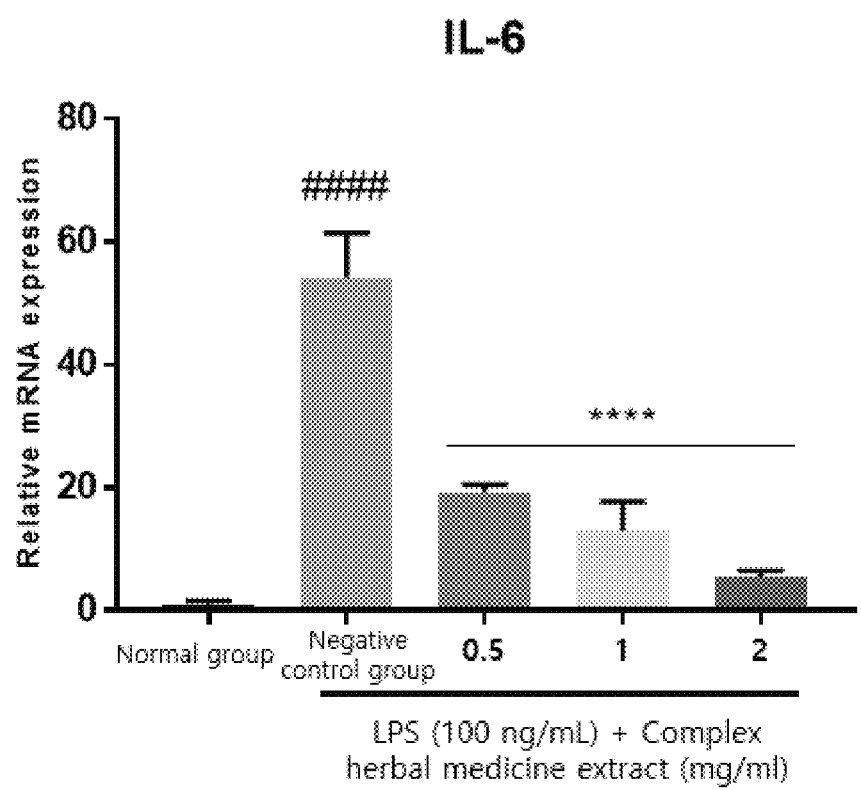
FIGS. 6A, 6B and 6C show the expression degrees of the inflammatory factors (IL-6, IL-1β, and iNOS) according to the treatment concentrations (0.5, 1, and 2 mg/mL) of the complex herbal medicine extract in the mouse macrophage cell line treated with LPS, in order to investigate the anti-inflammatory effect of the complex extract of three kinds of herbal medicines in Preparative Example 2 of the present disclosure.
Figure 6B:
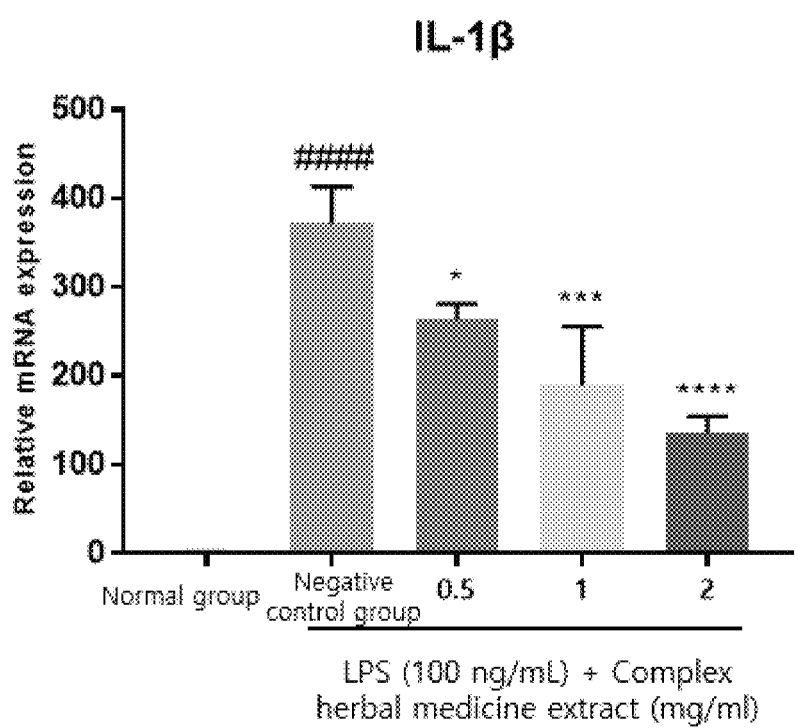
Figure 6C:
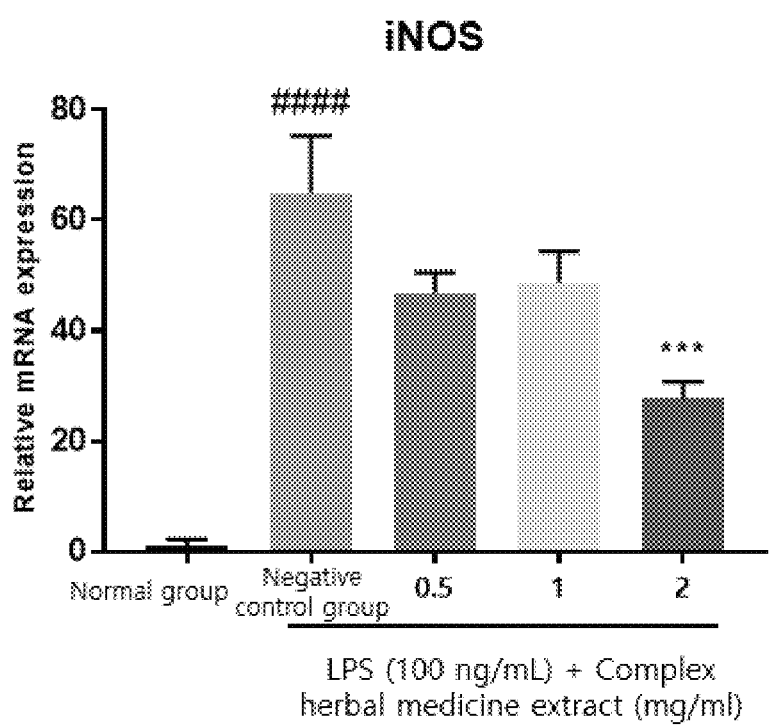

Test Example 6: Inflammatory Factor Expression Inhibitory Effect (Anti-Inflammatory Effect) of Complex Extract of Three Kinds of Herbal Medicines in Macrophage Cell Line Induced by LPS The mouse macrophage cell line Raw 264.7 cells (ATCC, USA) were incubated in the incubator of 5% $CO_2$ and 37° C. by using RPMI media (Invitrogen, USA) containing 10% fetal bovine serum (FBS). The cells were prepared on a 24-well plate at $2.5 \times 10^5$ cells per well, and stabilized. After 24 hours, the cell supernatant was removed, and then the cells were treated with 100 ng/mL LPS and the complex extract of three kinds of herbal medicines in Preparative Example 2 at concentrations of 0.5, 1, and 2 mg/mL. After 24 hours, the cell supernatant was removed, and then RNA was separated from the cells by using TRIzol (Invitrogen, USA). Thereafter, cDNA obtained through RT-PCR was used to perform qPCR using primers specific to the inflammatory factors IL-6, IL-1β, and iNOS and the SYBR green probe (Takara, Japan). The RNA expression change value obtained from qPCR was expressed as a relative change of GAPDH mRNA as a standard gene compared with a non-treatment group (FIG. 6). The primer sequences for mouse genes used in the test are shown in Table 4.

TABLE 4

| Gene | Direction | Nucleotide Sequence (5' to 3') | SEQ ID NO |
|---|---|---|---|
| GAPDH | Forward | AGCCTCGTCCCGTAGACAA | 1 |
|  | Reverse | AATCTCCACTTTGCCACTGC | 2 |
| IL-6 | Forward | TTGGTCCTTAGCCACTCCTTC | 3 |
|  | Reverse | TAGTCCTTCCTACCCCAATTTCC | 4 |
| IL-1β | Forward | TGTGCAAGTGTCTGAAGCAGC | 5 |
|  | Reverse | TGGAAGCAGCCCTTCATCTT | 6 |
| iNOS | Forward | CGAAACGCTTCACTTCCAA | 7 |
|  | Reverse | TGAGCCTATATTGCTGTGGCT | 8 |

As shown in FIG. 6, the production of the inflammatory factors IL-6, IL-1β, and iNOS significantly increased in the macrophages by LPS treatment (negative control group), and in the test groups treated with the complex extracts of three kinds of herbal medicines at concentrations of 0.5, 1, and 2 mg/ml together with LPS, all the expression levels of IL-6, IL-1β, and iNOS were significantly reduced in a dose-dependent manner. It can be therefore seen that the complex extracts of three kinds of herbal medicines of the present disclosure showed an excellent anti-inflammatory effect.

Figure 7:
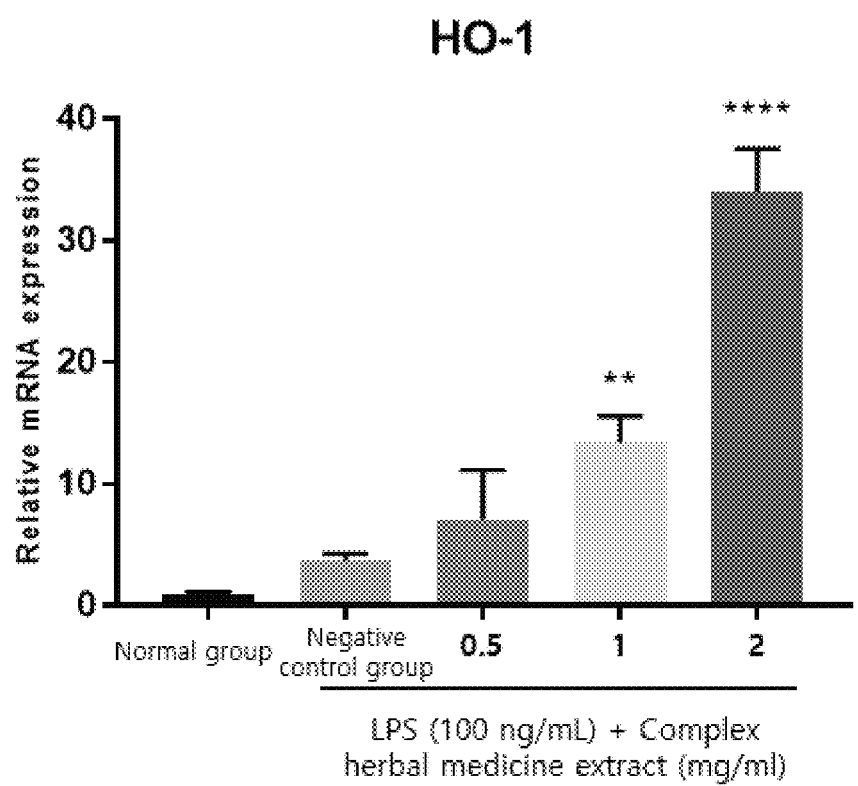
FIG. 7 shows the expression degrees of the anti-oxidative factor (HO-1) according to the treatment concentrations (0.5, 1, and 2 mg/mL) of the complex herbal medicine extract in the mouse macrophage cell line treated with LPS, in order to investigate the anti-oxidative effect of the complex extract of three kinds of herbal medicines in Preparative Example 2 of the present disclosure.

Test Example 7: Antioxidative Factor Expression Increasing Effect (Antioxidative Effect) of Complex Extract of Three Kinds of Herbal Medicines in Macrophage Cell Line Induced by LPS In order to investigate the effect of the complex extract of three kinds of herbal medicines of the present disclosure prepared in Preparative Example 2 on the expression of the antioxidative factor heme oxygenase-1 (HO-1) in macrophages induced by LPS, the test was carried out by the same method as in Test Example 6 except that qPCR was performed by using primers specific to HO-1 and SYBR green probe (Takara, Japan). The RNA expression change value obtained from the qPCR results was expressed as a relative change of GAPDH mRNA as a standard gene compared with a non-treatment group (FIG. 7). The primer sequences for mouse genes used in the test are shown in Table 5.

TABLE 5

| Gene | Direction | Nucleotide Sequence (5' to 3') | SEQ ID NO |
|---|---|---|---|
| GAPDH | Forward | AGCCTCGTCCCGTAGACAA | 1 |
|  | Reverse | AATCTCCACTTTGCCACTGC | 2 |
| HO-1 | Forward | CAGGTGATGCTGACAGAGGA | 9 |
|  | Reverse | GAGAGTGAGGACCCACTGGA | 10 |

As shown in FIG. 7, in the test groups treated with the complex extracts of three kinds of herbal medicines at concentrations of 0.5, 1, and 2 mg/ml together with LPS, the expression level of HO-1 significantly increased in a dose-dependent manner. It can be therefore seen that the complex extracts of three kinds of herbal medicines of the present disclosure showed an excellent antioxidative effect.

Test Example 8: Inflammatory Factor Expression Inhibitory and Antioxidative Factor Expression Increasing Effects (Anti-Inflammatory and Antioxidative Effects) of Complex Herbal Medicine Extract According to Mixing Ratio in Macrophage Cell Line Treated with LPS In order to investigate anti-inflammatory and antioxidative effects of the complex extracts of three kinds of herbal medicines in Preparative Example 3 according to the ratio in the macrophage cell line induced by LPS (Sigma, US), qPCR was performed by using the primers specific to IL-6, IL-1β, iNOS, and HO-1 genes and the SYBR green probe (Takara, Japan). The detailed test procedure was the same as in Test Examples 6 and 7, and the primer sequences for the mouse genes used in the test are shown in Tables 4 and 5 above.

Figure 8A:
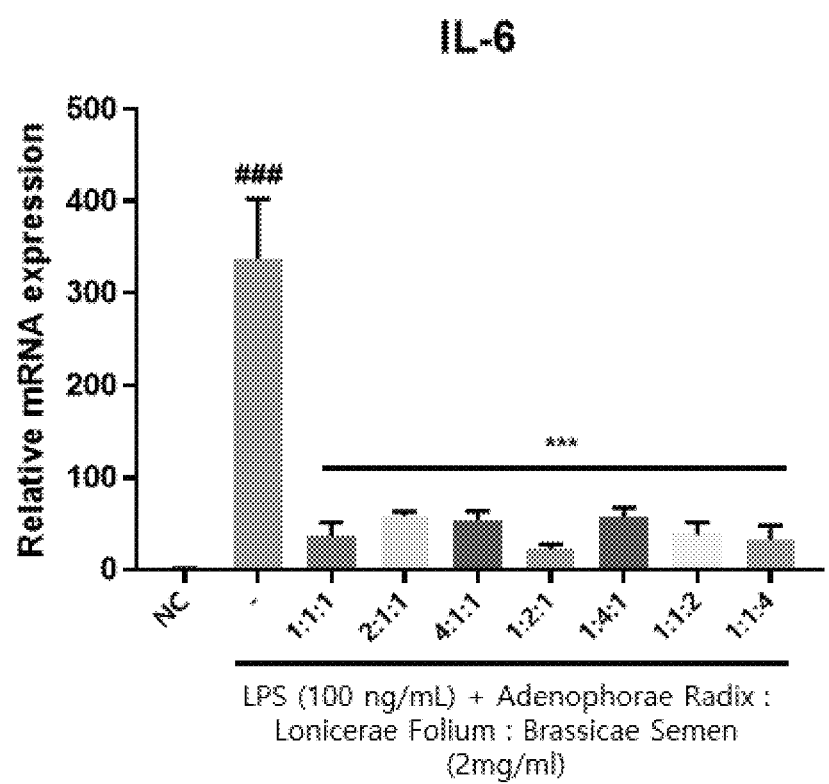
FIGS. 8A, 8B, 8C and 8D are graphs showing the expression degrees of the inflammatory factors (IL-6, IL-1β, and iNOS) and the anti-oxidative factor (HO-1) in the mouse macrophage cell line treated with LPS, in order to investigate the anti-inflammatory effect and the anti-oxidative effect according to the mixing ratio of the complex extract of three kinds of herbal medicines of the present disclosure.
Figure 8B:
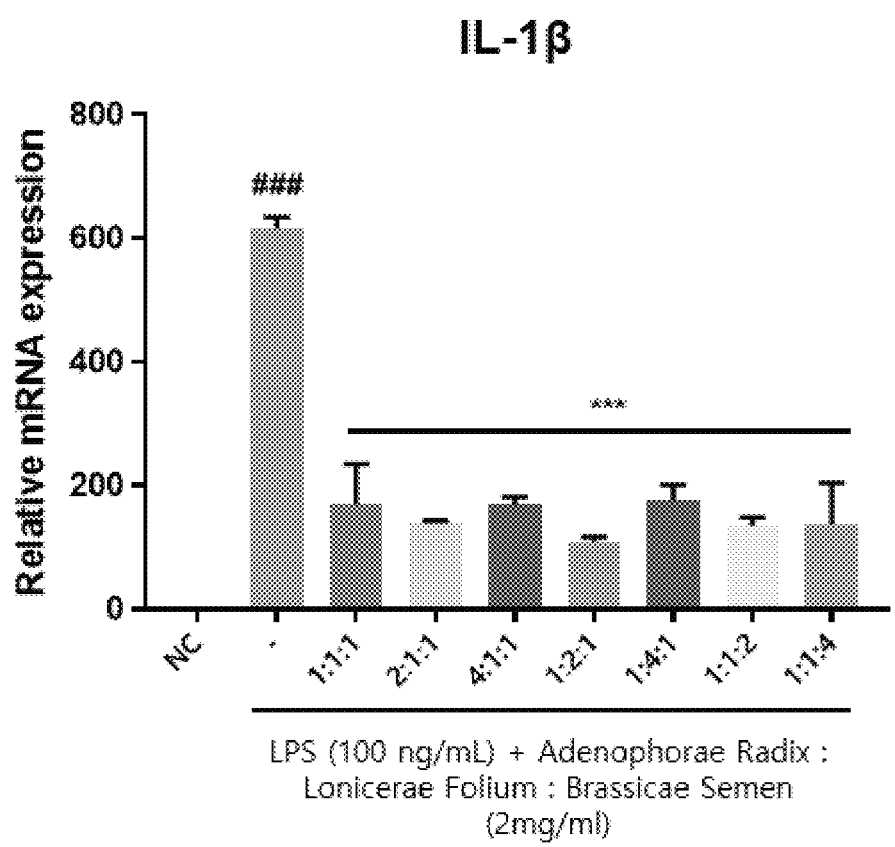
Figure 8C:
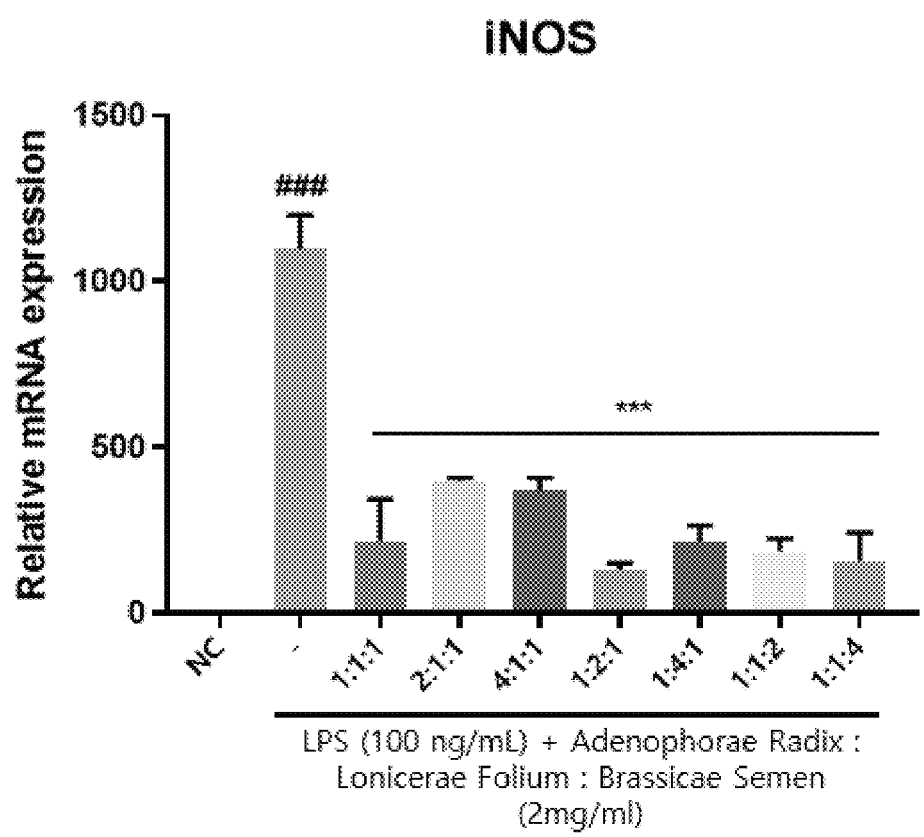
Figure 8D:
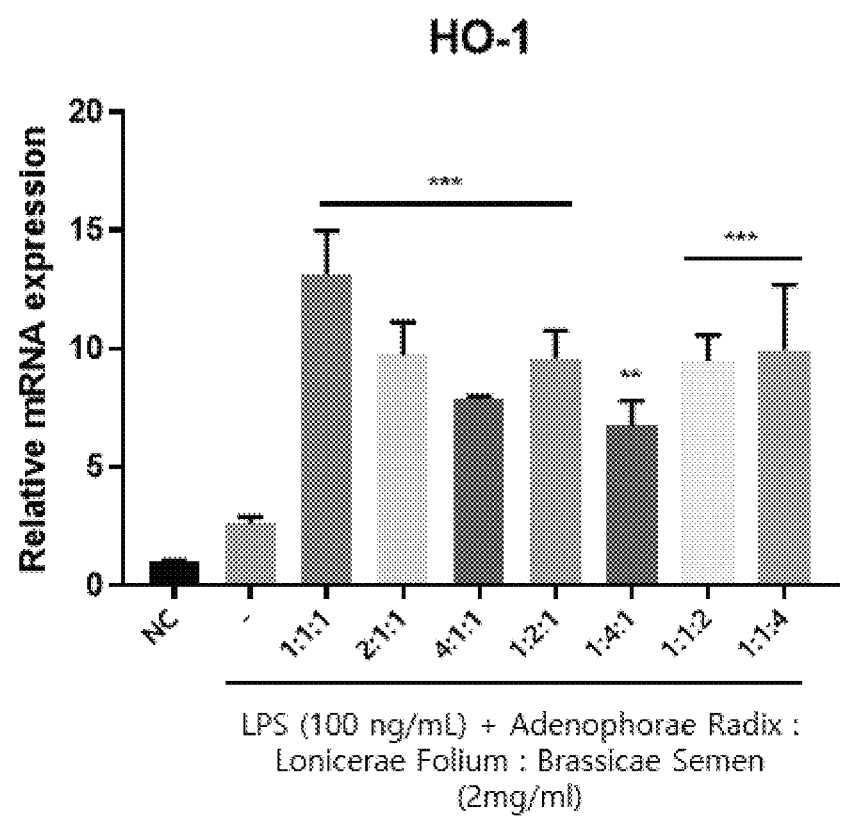

As shown in FIGS. 8a to 8c, the production of the inflammatory factors IL-6, IL-1β, and iNOS significantly increased in the macrophage cell line by LPS treatment (negative control group), and the expression levels of all the inflammatory factors showed significant reductions in the test groups treated with the complex extracts of three kinds of herbal medicines in Preparative Example 3 at a concentration of 2 mg/ml together with LPS. It can be therefore seen that the complex herbal medicine extract of the present disclosure showed an excellent anti-inflammatory effect. In the test groups treated with the complex herbal medicine extracts in Preparative Example 3 at a concentration of 2 mg/ml together with LPS, the expression level of the antioxidative factor HO-1 significantly increased (FIG. 8d). It can be therefore seen that the complex herbal medicine extracts of the present disclosure showed an excellent antioxidative effect.

Test Example 9: Anti-inflammatory and Antioxidative Effects of Complex Herbal Medicine Extract According to Hot-Water Extraction and the Concentrations of Extraction Solvent (Ethanol) in Macrophage Cell Line Induced by LPS In order to investigate anti-inflammatory and antioxidative effects of the complex herbal medicine extracts in Preparative Example 4 according to the concentration of an extraction solvent (ethanol) and the hot-water complex herbal medicine extract in Preparative Example 5, qPCR was performed by using the primers specific to IL-6, iNOS, and HO-1 and the SYBR green probe (Takara, Japan). The detailed test procedure was the same as in Test Examples 6 and 7, and the primer sequences for the mouse genes used in the test are shown in Tables 4 and 5 above.

Figure 9A:
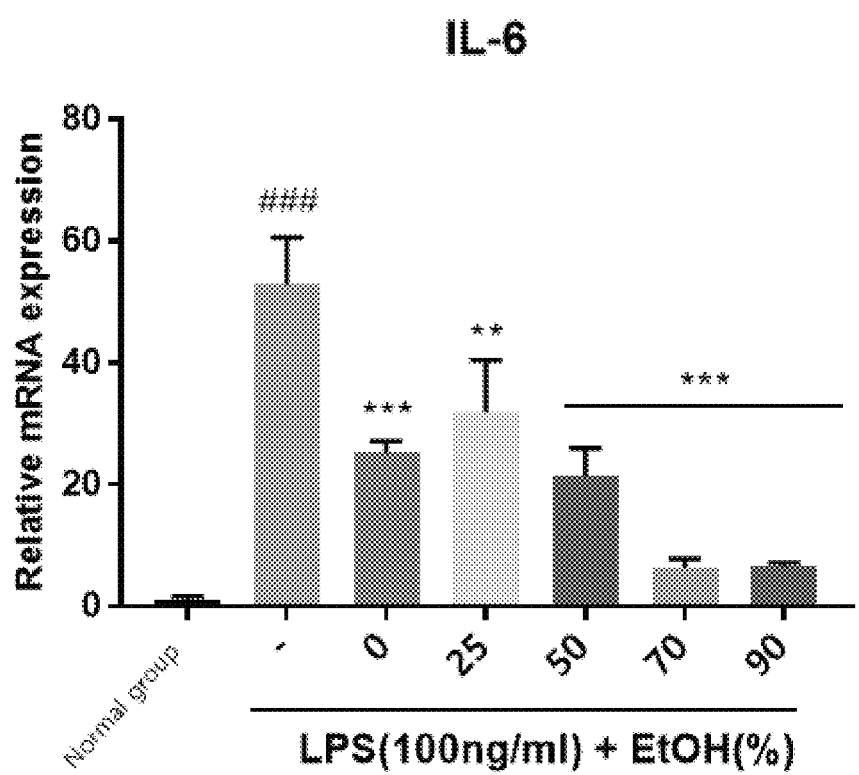
FIGS. 9A, 9B and 9C are graphs showing the expression levels of the inflammatory factors (IL-6 and iNOS) and the anti-oxidative factor (HO-1) according to the extraction method (hot-water extraction, 0%) and the concentrations (25, 50, 70, and 90%) of the extraction solvent (ethanol) in the mouse macrophage cell line treated with LPS, in order to investigate the anti-inflammatory effect and the anti-oxidative effect according to the extraction method(hot-water extraction) of the complex herbal medicine extract and the concentration of the extraction solvent (ethanol) of the present disclosure.
Figure 9B:
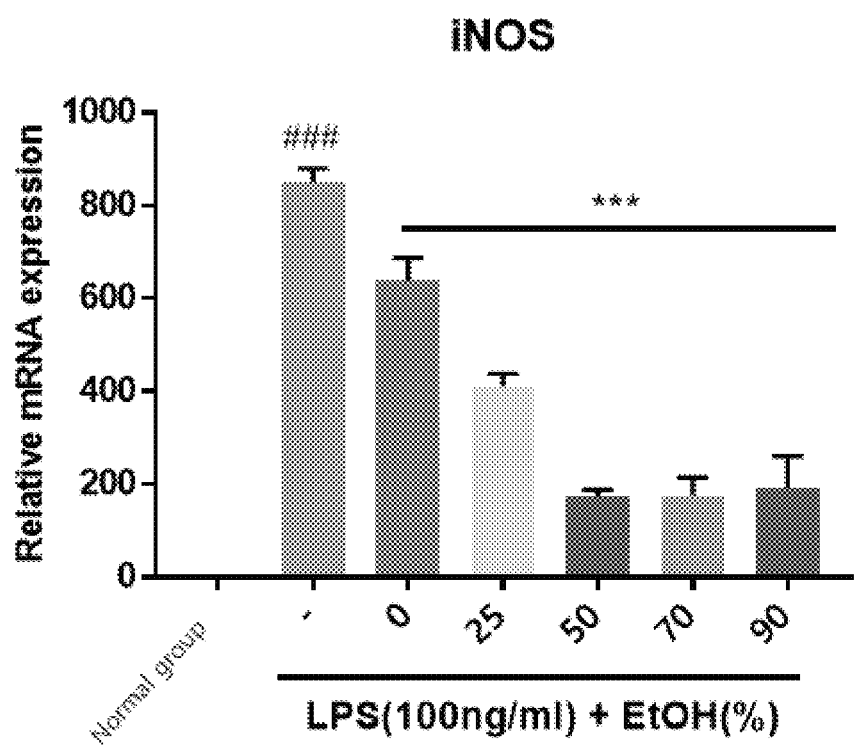
Figure 9C:
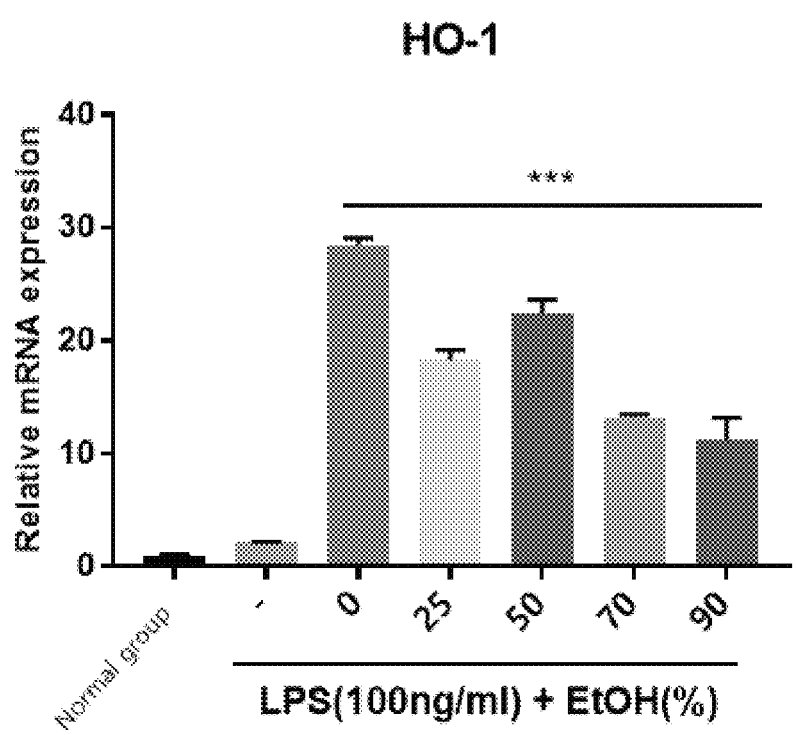

As shown in FIGS. 9a to 9b, the production of the inflammatory factors IL-6, and iNOS significantly increased in the macrophage cell line by LPS treatment (negative control group), and the expression levels of all the inflammatory factors showed significant reductions in the test groups treated with the complex herbal medicine extracts in Preparative Examples 4 and 5 at a concentration of 2 mg/ml together with LPS. It can be therefore seen that the complex herbal medicine extracts of the present disclosure showed an excellent anti-inflammatory effect. In the test groups treated with the complex herbal medicine extracts in Preparative Examples 4 and 5 at a concentration of 2 mg/ml together with LPS, the expression level of the antioxidative factor HO-1 significantly increased (FIG. 9c). It can be therefore seen that the complex herbal medicine extracts of the present disclosure showed an excellent antioxidative effect.

Test Example 10: Anti-Inflammatory Effects of Single Herbal Medicine Extract and Complex Herbal Medicine Extract in Pulmonary Inflammation Mouse Model Induced by LPS In order to investigate the pulmonary inflammation inhibitory effect of single and complex extracts of three kinds of herbal medicines, the following test was carried out. After 7-week-old male C57BL/6 mice (Raonbio, Korea) were acclimated for at least one week, the animals were classified into (1) a normal group, (2) a group with LPS induction and distilled water administration (negative control group), (3) to (5) groups with LPS induction and single herbal medicine extract administration, and (6) a group with LPS induction and complex herbal medicine extract administration.

The complex extract of three kinds of herbal medicines in Preparative Example 2 dissolved in distilled water and the single extracts of three kinds of herbal medicines in Comparative Example 1 dissolved in distilled water were orally administered to the test groups of (3) to (6) at 500 mg/kg once/day for five days, and only distilled water was orally administered to the normal group and the negative control group.

The induction of acute pulmonary inflammation in the test groups and the negative control group was performed by administering 50 μg of LPS (Sigma, US) dissolved in 50 μl of phosphate buffered saline (PBS) as a single drop into the mouse trachea 24 hours before the end of the test. For the normal group, phosphate buffered saline (PBS) was administered as a single drop into the mouse trachea.

After the last administration of the herbal medicine extracts or distilled water, the mice were sacrificed with carbon dioxide, and then the lung tissue was separated, and RNA was extracted by using TRIzol (Invitrogen, USA). Thereafter, cDNA obtained through RT-PCR was used to perform qPCR using primers specific to the inflammatory factors IL-1β, IL-6, and TNF-α and the SYBR green probe (Takara, Japan). The RNA expression change value obtained from qPCR was expressed as a relative change of GAPDH mRNA as a standard gene compared with a non-treatment group. The primer sequences for mouse genes used in the test are shown in Table 6.

TABLE 6

| Gene | Direction | Nucleotide Sequence (5' to 3') | SEQ ID NO |
|---|---|---|---|
| GAPDH | Forward | AGCCTCGTCCCGTAGACAA | 1 |
|  | Reverse | AATCTCCACTTTGCCACTGC | 2 |
| IL-6 | Forward | TTGGTCCTTAGCCACTCCTTC | 3 |
|  | Reverse | TAGTCCTTCCTACCCCAATTTCC | 4 |
| IL-1β | Forward | TGTGCAAGTGTCTGAAGCAGC | 5 |
|  | Reverse | TGGAAGCAGCCCTTCATCTT | 6 |
| TNF-α | Forward | AAGCCTGTAGCCCACGTCGTA | 11 |
|  | Reverse | GGCACCACTAGTTGGTTGTCTTTG | 12 |

Figure 10A:
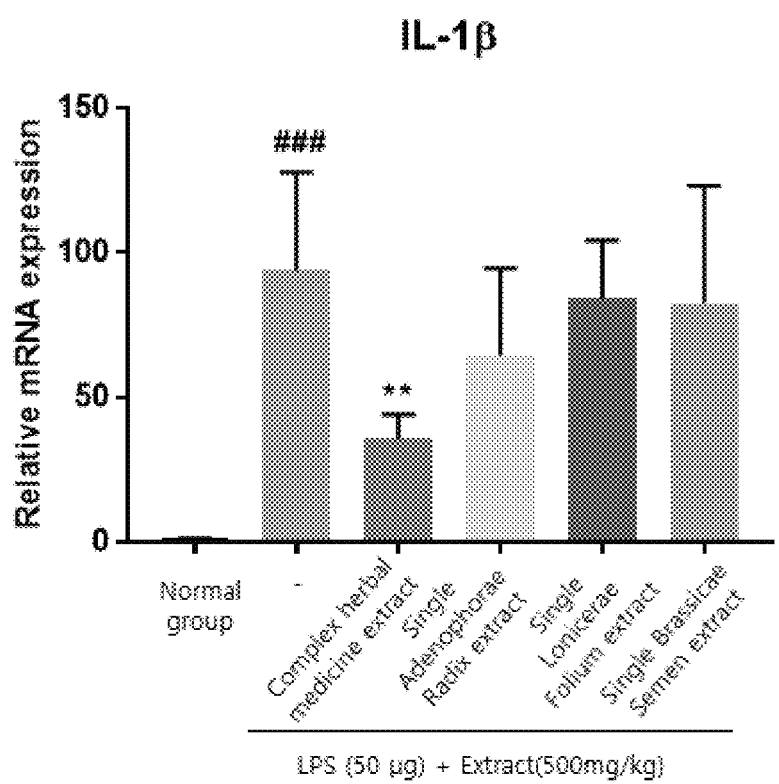
FIGS. 10A, 10B and 10C are graphs showing the expression levels of the inflammatory factors (IL-1β, IL-6, and TNF-α) according to the treatment with the single extracts of herbal medicines (Adenophorae Radix, Lonicerae Folium, and Brassicae Semen) and the complex extract of herbal medicines in the pulmonary inflammation mouse models induced by LPS, in order to investigate the pulmonary inflammation inhibitory effect of the single extracts and complex extract of herbal medicines.
Figure 10B:
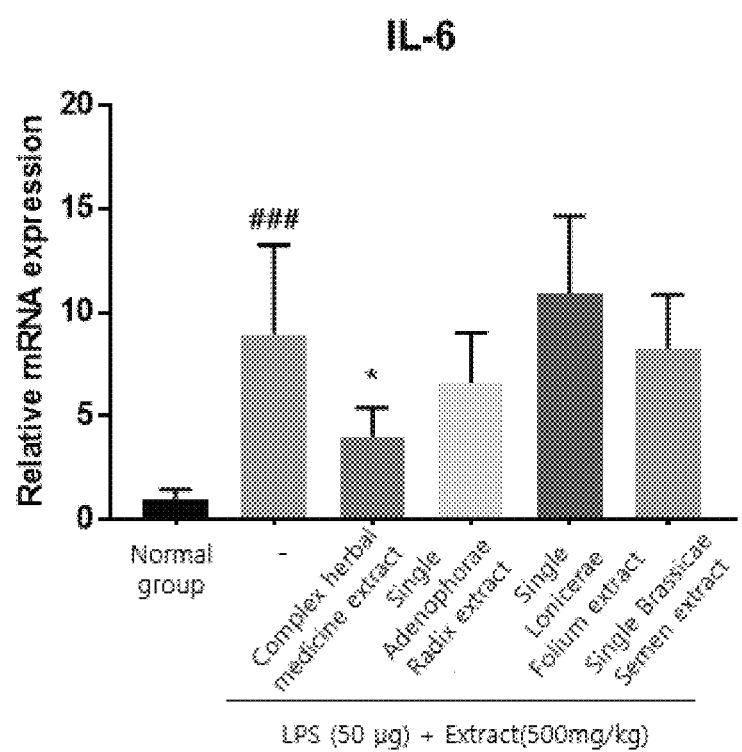
Figure 10C:
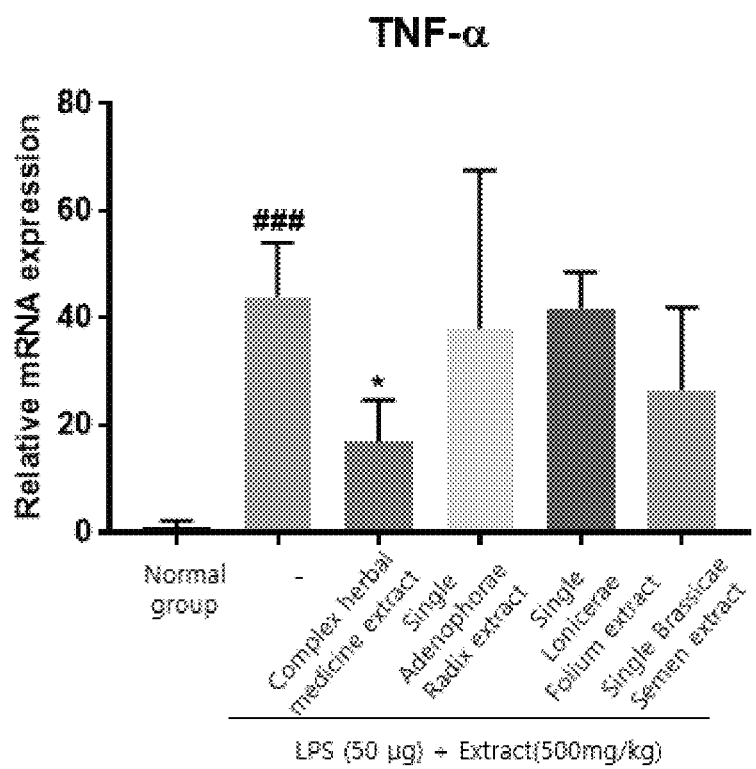

As shown in FIGS. 10a to 10c, the production of the inflammatory factors IL-1β, IL-6, and TNF-α significantly increased in the mouse lung tissue by LPS administration (negative control group), and in the test group with the administration of the complex herbal medicine extract in Preparative Example 2 together with LPS administration, the expression of the inflammatory factors are reduced, indicating an excellent anti-inflammatory effect. Whereas, the test groups with administration of single herbal medicine extracts together with LPS showed no significant reduction in inflammatory factors. It can be therefore seen that the anti-inflammatory effect of the complex herbal medicine extract of the present disclosure showed a synergistic effect compared with the single herbal medicine extracts, and thus was significantly excellent.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for prevention, alleviation, or treatment of a respiratory disease comprising:
   administering a composition to a subject in need thereof, the composition comprising, as an active ingredient, a therapeutically effective amount of a mixed extract consisting of: i) a Brassicae Semen extract, an Adenophorae Radix extract, and a Lonicerae Folium extract; or ii) a Brassicae Semen extract, an Adenophorae Radix extract, a Lonicerae Folium extract, and a Perillae Semen extract,
   wherein the extracts are obtained by extraction with ethanol or aqueous solution thereof.

2. The method of claim 1, wherein the respiratory disease is selected from the group consisting of a cold, rhinitis, pharyngitis, laryngitis, pharyngolaryngitis, pneumonia, acute or chronic bronchitis, asthma, and chronic obstructive pulmonary disease.

3. The method of claim 1, wherein the composition comprising as an active ingredient, a therapeutically effective amount of a mixed extract consisting of:
   i) a Brassicae Semen extract, an Adenophorae Radix extract, and a Lonicerae Folium extract, wherein the Brassicae Semen extract, the Adenophorae Radix extract, and the Lonicerae Folium extract are in a weight ratio of 1-4:1-4:1-4; or
   ii) a Brassicae Semen extract, an Adenophorae Radix extract, Lonicerae Folium extract, and a Perillae Semen extract, wherein the Brassicae Semen extract, the Adenophorae Radix extract, the Lonicerae Folium extract, the Perillae Semen extract are in a weight ratio of 1-4:1-4:1-4:1-4.

4. The method of claim 1, wherein the composition comprising as an active ingredient, a therapeutically effective amount of a mixed extract consisting of:
   i) a Brassicae Semen extract, an Adenophorae Radix extract, and a Lonicerae Folium extract, wherein the Brassicae Semen extract, the Adenophorae Radix extract, and the Lonicerae Folium extract are in a weight ratio of 1-4:1:1-4; or
   ii) a Brassicae Semen extract, an Adenophorae Radix extract, Lonicerae Folium extract, and a Perillae Semen extract, wherein the Brassicae Semen extract, the Adenophorae Radix extract, the Lonicerae Folium extract, the Perillae Semen extract are in a weight ratio of 1-4:1:1-4:1-4.

* * * * *